(12) United States Patent
Endo

(10) Patent No.: US 11,478,136 B2
(45) Date of Patent: Oct. 25, 2022

(54) ENDOSCOPE SYSTEM AND OPERATION METHOD THEREFOR

(71) Applicant: FUJIFILM Corporation, Tokyo (JP)

(72) Inventor: Maiko Endo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 688 days.

(21) Appl. No.: 16/548,431

(22) Filed: Aug. 22, 2019

(65) Prior Publication Data

US 2019/0374093 A1 Dec. 12, 2019

Related U.S. Application Data

(63) Continuation of application No. PCT/JP2017/046286, filed on Dec. 25, 2017.

(30) Foreign Application Priority Data

Mar. 6, 2017 (JP) .............................. JP2017-041221

(51) Int. Cl.
*A61B 1/015* (2006.01)
*A61B 1/045* (2006.01)
(Continued)

(52) U.S. Cl.
CPC .............. *A61B 1/015* (2013.01); *A61B 1/045* (2013.01); *A61B 5/1032* (2013.01);
(Continued)

(58) Field of Classification Search
CPC ................................................. A61B 1/00015
(Continued)

(56) References Cited

U.S. PATENT DOCUMENTS 11,259,692 B2 * 3/2022 Yamamoto ....... A61B 1/000095
2011/0230715 A1 9/2011 Saito
(Continued)

FOREIGN PATENT DOCUMENTS

EP 2912992 A1 9/2015
EP 3005933 A1 4/2016
(Continued)

OTHER PUBLICATIONS

European Communication pursuant to Article 94(3) EPC for European Application No. 17899353.1. dated Mar. 10, 2021.
(Continued)

*Primary Examiner* — Jerome Grant, II
(74) *Attorney, Agent, or Firm* — Birch, Stewart, Kolasch & Birch, LLP

(57) ABSTRACT

An endoscope system and an operation method therefor in which information regarding a residual liquid is obtained to efficiently remove the residual liquid are provided. On the basis of image signals in a plurality of wavelength ranges, baseline information that is information regarding a light scattering characteristic or a light absorption characteristic of an observation target and that does not depend on specific biological information is calculated. A baseline correction value for adjusting the baseline information to reference baseline information that is a reference for evaluating the baseline information is calculated. From the baseline correction value, residual liquid information regarding a residual liquid included in the observation target is calculated.

20 Claims, 20 Drawing Sheets

(51) Int. Cl.
  *A61B 5/103* (2006.01)
  *A61B 5/107* (2006.01)
  *A61B 5/145* (2006.01)
  *A61B 5/1455* (2006.01)

(52) U.S. Cl.
  CPC ........ *A61B 5/1075* (2013.01); *A61B 5/14546* (2013.01); *A61B 5/14551* (2013.01)

(58) Field of Classification Search
  USPC ......................................................... 600/109
  See application file for complete search history.

(56) References Cited

U.S. PATENT DOCUMENTS

| | | |
|---|---|---|
| 2015/0238126 A1 | 8/2015 | Saito |
| 2016/0183774 A1 | 6/2016 | Shiraishi |
| 2017/0014055 A1 | 1/2017 | Otani |
| 2018/0020903 A1 | 1/2018 | Saito |
| 2018/0146847 A1 | 5/2018 | Otsuka |
| 2018/0317754 A1 | 11/2018 | Yamamoto |
| 2019/0357759 A1* | 11/2019 | Yamamoto ............. A61B 1/005 |

FOREIGN PATENT DOCUMENTS

| | | | |
|---|---|---|---|
| EP | 3427637 A1 | 1/2019 | |
| JP | 2011-194028 A | 10/2011 | |
| JP | 2015-66127 A | 4/2015 | |
| JP | 2015-177961 A | 10/2015 | |
| JP | 2017-18503 A | 1/2017 | |
| JP | 2017-158782 A | 9/2017 | |
| JP | 7021183 * | 2/2022 | ......... A61B 1/00045 |
| WO | WO 2016/158276 A1 | 10/2016 | |
| WO | WO 2017/010013 A1 | 1/2017 | |
| WO | WO2018159082 A1 * | 9/2018 | ............. A61B 1/045 |

OTHER PUBLICATIONS

Extended European Search Report, dated Feb. 6, 2020, for European Application No. 17899353.1.

International Preliminary Report on Patentability and English translation of the Written Opinion of the International Searching Authority (Forms PCT/IB/326, PCT/IB/373, and PCT/ISA/237) for International Application No. PCT/JP2017/046286, dated Sep. 19, 2019.

International Search Report (Form PCT/ISA/210) for International Application No. PCT/JP2017/046286, dated Mar. 20, 2018, with English translation.

* cited by examiner

FIG. 5

| ILLUMINATION | IMAGE CAPTURE (IMAGE SIGNALS) |
|---|---|
| EMISSION OF FIRST BLUE LIGHT<br>EMISSION OF GREEN LIGHT<br>EMISSION OF RED LIGHT | (Bc, Gc, Rc) |

FIG. 6

| ILLUMINATION | | IMAGE CAPTURE (IMAGE SIGNALS) | |
|---|---|---|---|
| FIRST MEASUREMENT LIGHT EMISSION MODE | EMISSION OF SECOND BLUE LIGHT | FIRST MEASUREMENT IMAGE CAPTURE MODE | (B1, G1, R1) |
| SECOND MEASUREMENT LIGHT EMISSION MODE | EMISSION OF FIRST BLUE LIGHT<br>EMISSION OF GREEN LIGHT<br>EMISSION OF RED LIGHT | SECOND MEASUREMENT IMAGE CAPTURE MODE | (B2, G2, R2) |

FIG. 7

| | ILLUMINATION | | IMAGE CAPTURE (IMAGE SIGNALS) |
|---|---|---|---|
| FIRST CALIBRATION LIGHT EMISSION MODE | EMISSION OF FIRST BLUE LIGHT | FIRST CALIBRATION IMAGE CAPTURE MODE | (Bp, Gp, Rp) |
| SECOND CALIBRATION LIGHT EMISSION MODE | EMISSION OF SECOND BLUE LIGHT | SECOND CALIBRATION IMAGE CAPTURE MODE | (Bq, Gq, Rq) |
| THIRD CALIBRATION LIGHT EMISSION MODE | EMISSION OF GREEN LIGHT | THIRD CALIBRATION IMAGE CAPTURE MODE | (Br, Gr, Rr) |
| FOURTH CALIBRATION LIGHT EMISSION MODE | EMISSION OF RED LIGHT | FOURTH CALIBRATION IMAGE CAPTURE MODE | (Bs, Gs, Rs) |

ENDOSCOPE SYSTEM AND OPERATION METHOD THEREFOR

CROSS-REFERENCE TO RELATED APPLICATIONS

This application is a Continuation of PCT International Application No. PCT/JP2017/046286 filed on Dec. 25, 2017, which claims priority under 35 U.S.C § 119(a) to Japanese Patent Application No. 2017-041221 filed on Mar. 6, 2017. Each of the above application(s) is hereby expressly incorporated by reference, in its entirety, into the present application.

BACKGROUND OF THE INVENTION

1. Field of the Invention

The present invention relates to an endoscope system and an operation method therefor using biological function information such as the oxygen saturation level.

2. Description of the Related Art

In the medical field, it is a common practice to make diagnoses using an endoscope system that includes a light source device, an endoscope, and a processor device. Specifically, an endoscope system is widely used that not only captures images of an observation target but also controls the wavelength of illumination light to be radiated onto the observation target and performs signal processing, such as spectral estimation processing, on image signals obtained by image capturing of the observation target, thereby obtaining an observation image in which a specific tissue or structure, such as a blood vessel or a glandular tubular structure, is highlighted.

Further, currently, it is the case that biological function information is measured on the basis of image signals obtained by image capturing of an observation target, and the biological function information is used at the time of diagnosis. For example, it is known that a lesion, such as a cancer, is in a low-oxygen state. Therefore, the oxygen saturation level in the biological function information is measured and used in a diagnosis to thereby facilitate detection of the lesion (see JP2015-177961A and JP2011-194028A). However, it is known that, in a case where a residual liquid that includes a yellow pigment, such as bilirubin or stercobilin, exists in an observation target, the residual liquid affects the measurement accuracy of biological function information. Meanwhile, in JP2015-177961A, the oxygen saturation level can be accurately calculated even in a situation where a yellow pigment is adhered to an observation target.

SUMMARY OF THE INVENTION

As described above, in the case where a residual liquid including a yellow pigment, etc. exists in an observation target, the user is to supply water to remove the residual liquid. However, if the user does not know to what extent the user needs to remove the residual liquid in order to achieve satisfactory measurement accuracy of biological function information, such as the oxygen saturation level, a case may occur where the user takes time more than necessary to remove the residual liquid. In this case, the examination time using an endoscope increases, which is burdensome to the patient.

An object of the present invention is to provide an endoscope system and an operation method therefor in which information regarding a residual liquid is obtained to efficiently remove the residual liquid.

An endoscope system according to the present invention is an endoscope system including: a light source; an endoscope that performs image capturing of an observation target onto which illumination light emitted from the light source is radiated; and a processor device that performs system control and image processing, the endoscope system including: an image signal obtaining unit that obtains image signals in a plurality of wavelength ranges obtained by image capturing of the observation target; a baseline information calculation unit that calculates, on the basis of the image signals in the plurality of wavelength ranges, baseline information that is information regarding a light scattering characteristic or a light absorption characteristic of the observation target and that does not depend on specific biological information; a reference baseline information storage unit that stores in advance reference baseline information that is a reference for evaluating the baseline information; a baseline correction value calculation unit that calculates a baseline correction value for adjusting the baseline information to the reference baseline information; and a residual liquid information calculation unit that calculates residual liquid information regarding a residual liquid included in the observation target from the baseline correction value.

It is preferable that the endoscope system further include a first residual liquid image generation unit that generates a first residual liquid image representing distribution of the residual liquid information. It is preferable that the endoscope system further include a second residual liquid image generation unit that generates a second residual liquid image representing the residual liquid information by a numerical value or an indicator. It is preferable that the endoscope system further include: a biological information calculation unit that calculates the specific biological information; and a biological information calculation accuracy conversion unit that converts the residual liquid information to a calculation accuracy of the specific biological information. It is preferable that the endoscope system further include a residual liquid removal guidance image generation unit that generates, in accordance with the residual liquid information, a residual liquid removal guidance image for urging removal of the residual liquid. It is preferable that the endoscope system further include a residual liquid removal instruction unit that instructs, in accordance with the residual liquid information, a residual liquid removal part to remove the residual liquid, the residual liquid removal part being a part for removing the residual liquid. It is preferable that the residual liquid removal instruction unit set a residual liquid removal condition in accordance with the residual liquid information.

It is preferable that the residual liquid information calculation unit include a residual liquid amount calculation unit that calculates a residual liquid amount of the residual liquid as the residual liquid information. It is preferable that the residual liquid amount calculation unit calculate the residual liquid amount having an increased value as the baseline correction value increases. It is preferable that the endoscope further include a residual liquid removal part for removing the residual liquid, and that the residual liquid information calculation unit include a residual liquid removal ratio/ residual ratio calculation unit that calculates a pre-residual-liquid-removal residual liquid amount before removal of the residual liquid and a post-residual-liquid-removal residual liquid amount after removal of the residual liquid and that calculates at least one of a removal ratio of the residual liquid or a residual ratio of the residual liquid as the residual liquid information from the pre-residual-liquid-removal residual liquid amount and the post-residual-liquid-removal residual liquid amount. It is preferable that the residual liquid removal part remove the residual liquid by at least any of water supply, air supply, or suction.

It is preferable that the image signals in the plurality of wavelength ranges include a first image signal that corresponds to a first wavelength range in which a light absorption amount changes in accordance with a change in the specific biological information, a second image signal that corresponds to a second wavelength range that is a wavelength range different from the first wavelength range and in which a light absorption amount changes due to a factor other than a change in the specific biological information, a third image signal that corresponds to a third wavelength range that is longer in wavelength than the first wavelength range and the second wavelength range and in which a light absorption amount changes in accordance with a blood volume, and a fourth image signal that corresponds to a fourth wavelength range that is longer in wavelength than the third wavelength range. It is preferable that the first image signal, the second image signal, the third image signal, and the fourth image signal be obtained by multi-frame image capturing of the observation target.

It is preferable that the specific biological information change in accordance with a concentration of a hemoglobin pigment included in the observation target. It is preferable that the specific biological information be any of an oxygen saturation level, a blood vessel density, a blood vessel depth, a blood vessel thickness, or a blood concentration. It is preferable that the baseline information be information that changes in accordance with a concentration of a pigment other than hemoglobin included in the observation target. It is preferable that the pigment other than hemoglobin be a pigment that is included in a living body or that is used at a time of endoscopic observation. It is preferable that the pigment other than hemoglobin include at least any of a yellow pigment, a bluish violet series pigment, a brown series pigment, or a white pigment. It is preferable that the yellow pigment be bilirubin or stercobilin, the bluish violet series pigment be indigo carmine or crystal violet, the brown series pigment be Lugol, and the white pigment be acetic acid. It is preferable that the reference baseline information be baseline information obtained in a case where an effect of the pigment other than hemoglobin does not exist.

An operation method for an endoscope system according to the present invention is an operation method for an endoscope system including a light source, an endoscope that performs image capturing of an observation target onto which illumination light emitted from the light source is radiated, and a processor device that performs system control and image processing, the operation method having: a step of obtaining image signals in a plurality of wavelength ranges obtained by image capturing of the observation target, by an image signal obtaining unit; a step of calculating, on the basis of the image signals in the plurality of wavelength ranges, baseline information that is information regarding a light scattering characteristic or a light absorption characteristic of the observation target and that does not depend on specific biological information, by a baseline information calculation unit; a step of calculating a baseline correction value for adjusting the baseline information to reference baseline information that is a reference for evaluating the baseline information, by a baseline correction value calculation unit; and a step of calculating residual liquid information regarding a residual liquid included in the observation target from the baseline correction value, by a residual liquid information calculation unit.

According to the present invention, information regarding a residual liquid is obtained to efficiently remove the residual liquid.

BRIEF DESCRIPTION OF THE DRAWINGS

FIG. 5 is a diagram for explaining light emission of illumination light and image capturing of an observation target in a normal mode;

FIG. 6 is a diagram for explaining light emission of illumination light and image capturing of an observation target in an oxygen saturation mode;

FIG. 7 is a diagram for explaining light emission of illumination light and image capturing of an observation target in a calibration mode;

DESCRIPTION OF THE PREFERRED EMBODIMENTS

First Embodiment

Figure 1:
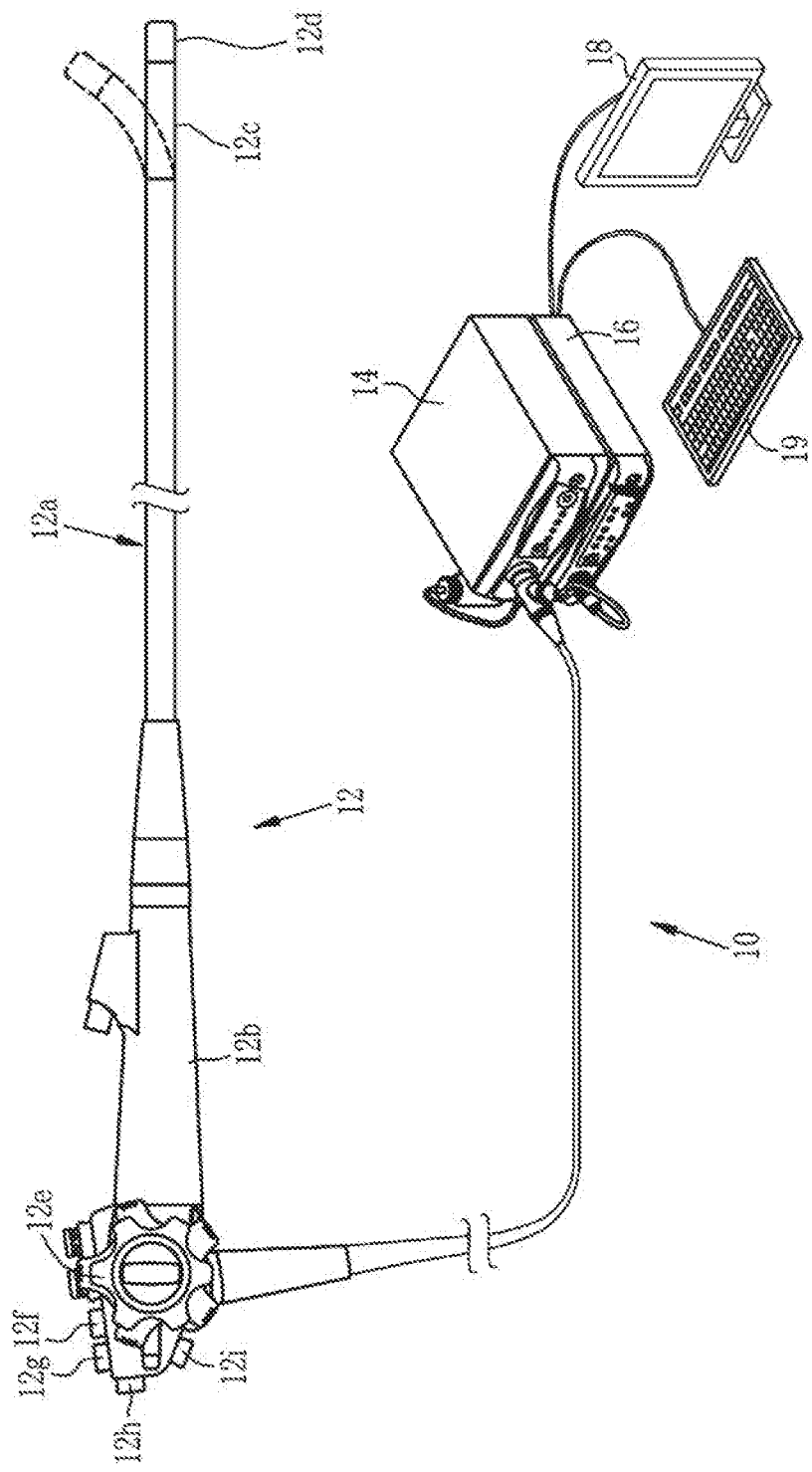
FIG. 1 is an external view of an endoscope system.

In FIG. 1, an endoscope system 10 has an endoscope 12, a light source device 14, a processor device 16, a monitor 18, and a console 19. The endoscope 12 is optically connected to the light source device 14 and electrically connected to the processor device 16. The endoscope 12 has an insertion part 12a that can be inserted into the body that is an observation target, an operation part 12b that is provided in the proximal end portion of the insertion part 12a, and a bending part 12c and a distal end part 12d that are provided on the distal end side of the insertion part 12a. The bending part 12c makes a bending motion in response to an operation of an angle knob 12e of the operation part 12b. The distal end part 12d is turned in an intended direction in association with the bending motion of the bending part 12c.

In the operation part 12b, in addition to the angle knob 12e, a mode switching SW (mode switching switch) 12f used in an operation of switching between observation modes, a still-image obtainment instruction part 12g used to give an instruction for obtaining a still image of an observation target, an air/water supply button 12h for causing air or water to jet from the distal end part 12d, and a suction button 12i for sucking a residual liquid, etc. on an observation target are provided.

Note that the endoscope system 10 has three observation modes, namely, a normal mode, an oxygen saturation mode, and a calibration mode. In the normal mode, a natural-color image (hereinafter referred to as a normal image) obtained by image capturing of an observation target using white light as illumination light is displayed on the monitor 18. In the oxygen saturation mode, the oxygen saturation level of an observation target is measured by using correlations between image signals obtained by image capturing of an observation target and oxygen saturation levels, and the measured oxygen saturation level is represented by an image using pseudo colors, etc. (hereinafter referred to as an oxygen saturation image), and the image is displayed on the monitor 18.

The calibration mode includes a residual liquid removal ratio/residual ratio mode in which the residual liquid amount of a residual liquid included in an observation target is calculated and the removal ratio, the residual ratio, etc. of the residual liquid are obtained from the calculated residual liquid amount of the residual liquid, and a correlation correction mode in which the correlations that are used to calculate the oxygen saturation level is corrected. Switching between these two modes is performed by using the mode switching SW (mode switching switch) 12f.

The processor device 16 is electrically connected to the monitor 18 and the console 19. The monitor 18 outputs and displays an image of an observation target, information associated with the image of the observation target, etc. The console 19 functions as a user interface that accepts operations of inputting functional settings, etc. Note that, to the processor device 16, an external recording unit (not illustrated) for recording images, image information, etc. may be connected.

Figure 2:
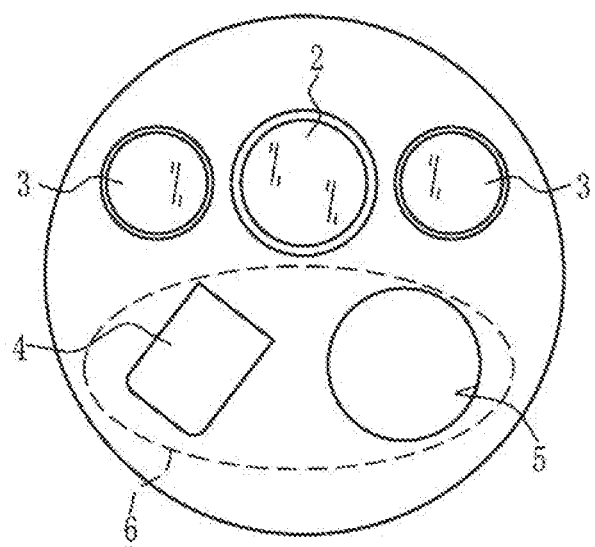
FIG. 2 is a plan view of a distal end surface of a distal end part of an endoscope.

As illustrated in FIG. 2, on the distal end surface of the distal end part 12d of the endoscope, an observation window 2, illumination windows 3, an air/water supply nozzle 4, and a forceps outlet 5 are provided. The observation window 2 is arranged in the center of one side of the distal end surface of the distal end part, and on the inner side of the observation window 2, the distal end part has an image sensor 44 (see FIG. 3) used to capture images of an observation target. The two illumination windows 3 are provided at positions so as to be symmetric about the observation window 2, and an observation target is illuminated with illumination light from the illumination windows 3. Through the air/water supply nozzle 4, air or water is made to jet to the observation window 2 for cleaning the observation window 2, and air or water is made to jet to an observation target, for example, after removal of a lesion. Through the forceps outlet 5, a treatment tool, etc. is exposed, and a residual liquid, etc. on an observation target is sucked. Note that the air/water supply nozzle 4 or the forceps outlet 5 is used to remove a residual liquid on an observation target, and therefore, constitutes a residual liquid removal part 6.

Figure 3:
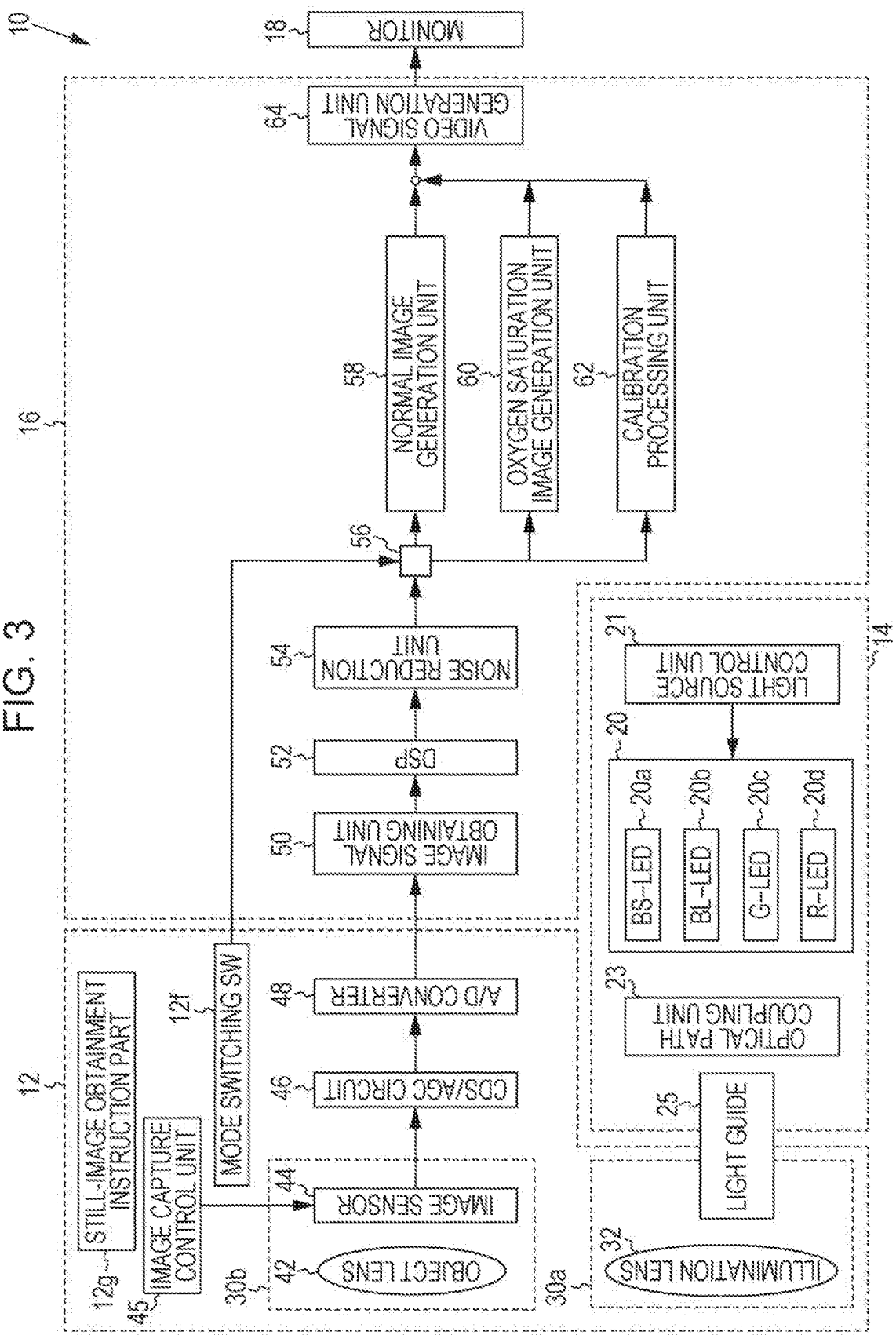
FIG. 3 is a block diagram illustrating functions of an endoscope system according to a first embodiment.

In FIG. 3, the light source device 14 includes a light source 20 and a light source control unit 21 that controls the light source 20. The light source 20 has, for example, a plurality of semiconductor light sources, and these light sources are each turned on or off. In a case of turn-on, the light emission amount of each semiconductor light source is controlled to emit illumination light with which an observation target is illuminated. In this embodiment, the light source 20 has LEDs of four colors, namely, a BS-LED (Blue Short-wavelength Light Emitting Diode) 20a, a BL-LED (Blue Long-wavelength Light Emitting Diode) 20b, a G-LED (Green Light Emitting Diode) 20c, and an R-LED (Red Light Emitting Diode) 20d.

The BS-LED 20a emits first blue light BS in a wavelength range of 450±10 nm. The BL-LED 20b emits second blue light BL in a wavelength range of 470±10 nm. The G-LED 20c emits green light G in a wavelength range of 540±10 nm. The R-LED 20d emits red light R in a wavelength range of 640±20 nm. Note that the center wavelength and the peak wavelength of each of the LEDs 20a to 20d may be the same or may be different. Note that nm is the abbreviation for nanometer.

The light source control unit 21 inputs control signals to the LEDs 20a to 20d individually to control turn-on or turn-off of the LEDs 20a to 20d and the light emission amounts thereof individually at the time of turn-on. Control for turn-on or turn-off by the light source control unit 21 differs depending on the mode. In the normal mode, the BS-LED 20a, the G-LED 20c, and the R-LED 20d are simultaneously turned on to emit the first blue light BS, the green light G, and the red light R simultaneously. In the oxygen saturation mode, a first measurement light emission mode in which the BL-LED 20b is turned on to emit the second blue light BL and a second measurement light emission mode in which the BS-LED 20a, the G-LED 20c, and the R-LED 20d are simultaneously turned on to emit the first blue light BS, the green light G, and the red light R simultaneously are alternately repeated.

In the calibration mode, the BS-LED 20a, the BL-LED 20b, the G-LED 20c, and the R-LED 20d are sequentially turned on to emit the first blue light BS, the second blue light BL, the green light G, and the red light R sequentially. In the calibration mode, a mode in which the first blue light BS is emitted is assumed to be a first calibration light emission mode, a mode in which the second blue light BL is emitted is assumed to be a second calibration light emission mode, a mode in which the green light G is emitted is assumed to be a third calibration light emission mode, and a mode in which the red light R is emitted is assumed to be a fourth calibration light emission mode.

Light emitted from each of the LEDs 20*a* to 20*d* enters a light guide 25 via an optical path coupling unit 23 constituted by a mirror, a lens, etc. The light guide 25 is built in the endoscope 12 and in a universal cord (a cord that connects the endoscope 12 with the light source device 14 and the processor device 16). Light from the optical path coupling unit 23 propagates through the light guide 25 up to the distal end part 12*d* of the endoscope 12.

In the distal end part 12*d* of the endoscope 12, an illumination optical system 30*a* and an image capture optical system 30*b* are provided. The illumination optical system 30*a* has an illumination lens 32, and illumination light propagating through the light guide 25 passes through the illumination lens 32 and is radiated onto an observation target. The image capture optical system 30*b* has an object lens 42 and the image sensor 44. Light from an observation target as a result of radiation of illumination light enters the image sensor 44 via the object lens 42. Accordingly, an image of the observation target is formed on the image sensor 44.

Figure 4:
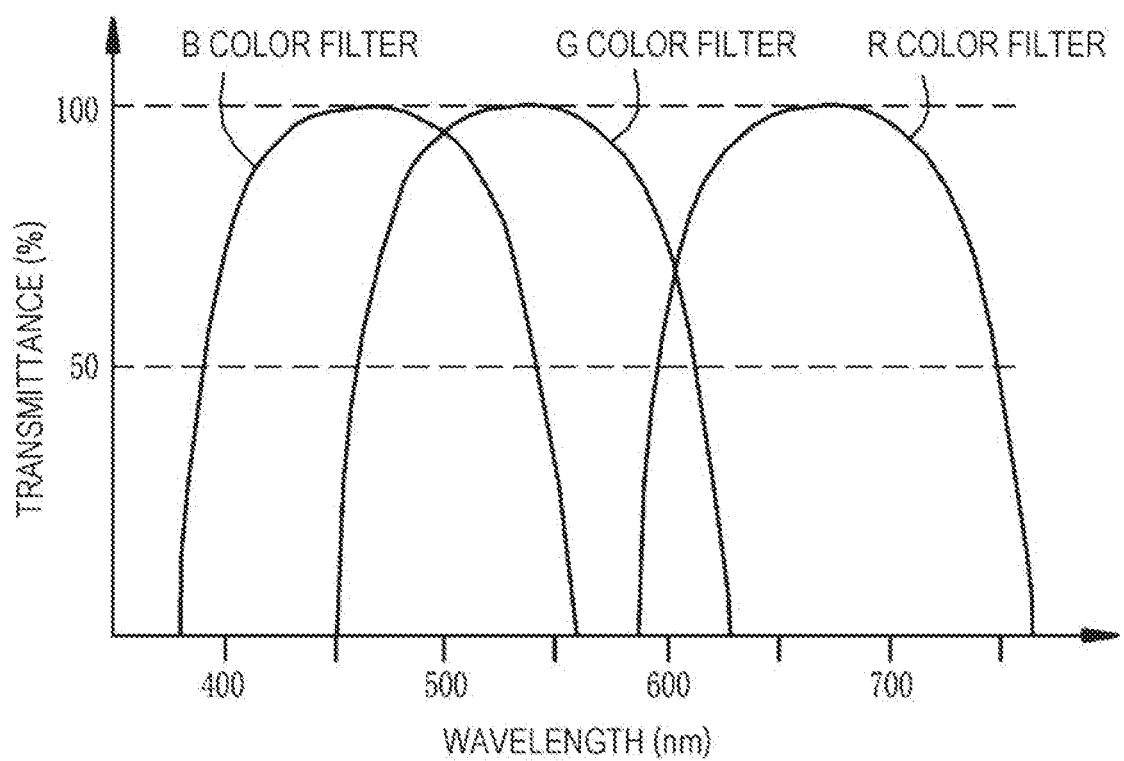
FIG. 4 is a graph illustrating the spectral sensitivity of an image sensor.

The image sensor 44 is a color image sensor used to capture images of an observation target that is being illuminated with illumination light. As each pixel of the image sensor 44, any of a B pixel (blue pixel) having a B (blue) color filter, a G pixel (green pixel) having a G (green) color filter, or an R pixel (red pixel) having an R (red) color filter is provided. As illustrated in FIG. 4, the B color filter mainly allows light in a blue-color range, specifically, light in a wavelength range of 380 to 560 nm, to pass therethrough. The peak wavelength at which the transmittance reaches its peak exists near 460 to 470 nm. The G color filter mainly allows light in a green-color range, specifically, light in a wavelength range of 450 to 630 nm, to pass therethrough. The R color filter mainly allows light in a red-color range, specifically, light in a wavelength range of 580 to 760 nm, to pass therethrough.

As the image sensor 44, a CCD (Charge Coupled Device) image sensor or a CMOS (Complementary Metal-Oxide Semiconductor) image sensor can be used. Instead of the image sensor 44, which is a primary-color image sensor, a complementary-color image sensor including complementary-color filters of C (cyan), M (magenta), Y (yellow), and G (green) may be used. In a case of using a complementary-color image sensor, image signals for four colors of C, M, Y, and G are output. Therefore, color conversion from complementary colors to primary colors is performed to convert the image signals for four colors of C, M, Y, and G to image signals for three colors of R, G, and B, so that image signals for respective colors of R, G, and B similar to those from the image sensor 44 can be obtained.

The image sensor 44 is driven and controlled by an image capture control unit 45. Control by the image capture control unit 45 differs depending on the mode. As illustrated in FIG. 5, in the normal mode, the image capture control unit 45 controls the image sensor 44 so that image capturing of an observation target that is being illuminated with the first blue light BS, the green light G, and the red light R is performed for each frame. Accordingly, a Bc image signal is output from each B pixel of the image sensor 44, a Gc image signal is output from each G pixel thereof, and an Rc image signal is output from each R pixel thereof As illustrated in FIG. 6, in the oxygen saturation mode, the image capture control unit 45 controls the image sensor 44 to alternately repeat a first measurement image capture mode in which image capturing of an observation target that is being illuminated with the second blue light BL in the first measurement light emission mode is performed for one frame and a second measurement image capture mode in which image capturing of the observation target that is being illuminated with the first blue light BS, the green light G, and the red light R in the second measurement light emission mode is performed for one frame. Accordingly, in the first measurement image capture mode, a B1 image signal is output from each B pixel of the image sensor 44, a G1 image signal is output from each G pixel thereof, and an R1 image signal is output from each R pixel thereof. Further, in the second measurement image capture mode, a B2 image signal is output from each B pixel of the image sensor 44, a G2 image signal is output from each G pixel thereof, and an R2 image signal is output from each R pixel thereof.

As illustrated in FIG. 7, in the calibration mode, multi-frame image capturing, namely, four-frame image capturing, of an observation target is performed. In the calibration mode, the image capture control unit 45 controls the image sensor 44 to sequentially perform a first calibration image capture mode in which image capturing of an observation target that is being illuminated with the first blue light BS in the first calibration light emission mode is performed for one frame, a second calibration image capture mode in which image capturing of the observation target that is being illuminated with the second blue light BL in the second calibration light emission mode is performed for one frame, a third calibration image capture mode in which image capturing of the observation target that is being illuminated with the green light G in the third calibration light emission mode is performed for one frame, and a fourth calibration image capture mode in which image capturing of the observation target that is being illuminated with the red light R in the fourth calibration light emission mode is performed for one frame.

Accordingly, in the first calibration image capture mode, a Bp image signal is output from each B pixel of the image sensor 44, a Gp image signal is output from each G pixel thereof, and an Rp image signal is output from each R pixel thereof. In the second calibration image capture mode, a Bq image signal is output from each B pixel of the image sensor 44, a Gq image signal is output from each G pixel thereof, and an Rq image signal is output from each R pixel thereof. In the third calibration image capture mode, a Br image signal is output from each B pixel of the image sensor 44, a Gr image signal is output from each G pixel thereof, and an Rr image signal is output from each R pixel thereof. In the fourth calibration image capture mode, a Bs image signal is output from each B pixel of the image sensor 44, a Gs image signal is output from each G pixel thereof, and an Rs image signal is output from each R pixel thereof.

A CDS/AGC (Correlated Double Sampling/Automatic Gain Control) circuit 46 performs correlated double sampling (CDS) or automatic gain control (AGC) on analog image signals obtained from the image sensor 44. The image signals that pass through the CDS/AGC circuit 46 are converted to digital image signals by an A/D (Analog/Digital) converter 48. The digital image signals after A/D conversion are input to the processor device 16.

The processor device 16 includes an image signal obtaining unit 50, a DSP (Digital Signal Processor) 52, a noise reduction unit 54, an image processing switch unit 56, a normal image generation unit 58, an oxygen saturation image generation unit 60, a calibration processing unit 62, and a video signal generation unit 64. The image signal obtaining unit 50 receives image signals input from the endoscope 12 and transmits the received image signals to the DSP 52.

The DSP 52 performs various types of signal processing including defect correction, offsetting, gain correction, linear matrix processing, gamma conversion, demosaicing, and YC conversion on the received image signals. In the defect correction, signals from defective pixels of the image sensor 44 are corrected. In the offsetting, a dark current component is removed from the image signals subjected to the defect correction, and an accurate zero level is set. In the gain correction, the image signals of respective colors after the offsetting are multiplied by specific gains to adjust the signal level of each image signal. For the image signals of respective colors after the gain correction, linear matrix processing for increasing color reproducibility is performed.

Thereafter, gamma conversion is performed to adjust the brightness and saturation of each image signal. The image signals after the linear matrix processing are subjected to demosaicing (also called isotropic processing or synchronization processing) to generate, for each pixel, signals of missing colors by interpolation. With the demosaicing, every pixel has signals of the respective colors of R, G, and B. The DSP 52 performs the YC conversion on each image signal after the demosaicing and outputs brightness signals Y, color difference signals Cb, and color difference signals Cr to the noise reduction unit 54.

The noise reduction unit 54 performs noise reduction processing using, for example, a moving average method or a median filter method for the image signals subjected to the demosaicing, etc. in the DSP 52. The image signals in which noise is reduced are input to the image processing switch unit 56.

The image processing switch unit 56 switches the transmission destination of the image signals from the noise reduction unit 54 to the normal image generation unit 58, the oxygen saturation image generation unit 60, or the calibration processing unit 62 in accordance with the set mode. Specifically, in a case where the normal mode is set, the image processing switch unit 56 inputs the image signals from the noise reduction unit 54 to the normal image generation unit 58. In a case where the oxygen saturation mode is set, the image processing switch unit 56 inputs the image signals from the noise reduction unit 54 to the oxygen saturation image generation unit 60. In a case where the calibration mode is set, the image processing switch unit 56 inputs the image signals from the noise reduction unit 54 to the calibration processing unit 62.

The normal image generation unit 58 performs further processing, namely, color conversion processing including 3×3 matrix processing, gradation transformation, three-dimensional LUT (Look-Up Table) processing, etc., for the input Rc image signals, Gc image signals, and Bc image signals for one frame. The normal image generation unit 58 performs various types of color enhancing processing on RGB image data subjected to the color conversion processing. The normal image generation unit 58 performs structure enhancement processing including spatial frequency enhancement on the RGB image data subjected to the color enhancement processing. The RGB image data subjected to the structure enhancement processing is input to the video signal generation unit 64 as a normal image.

The oxygen saturation image generation unit 60 uses correlations between oxygen saturation levels and the B1 image signals, the G2 image signals, and the R2 image signals among the image signals obtained in the oxygen saturation mode to calculate oxygen saturation levels. The method for calculating oxygen saturation levels will be described below. The calculated oxygen saturation levels are represented by an image using pseudo colors, etc. to generate an oxygen saturation image. The oxygen saturation image is input to the video signal generation unit 64.

In a case where the residual liquid removal ratio/residual ratio calculation mode is set, the calibration processing unit 62 calculates a baseline correction value from the Bp image signals (corresponding to "first image signal" of the present invention), the Bq image signals (corresponding to "second image signal" of the present invention), the Gr image signals (corresponding to "third image signal" of the present invention), and the Rs image signals (corresponding to "fourth image signal" of the present invention) among the image signals obtained in the calibration mode, calculates the residual liquid amount of a residual liquid, such as a yellow pigment, on the basis of the calculated baseline correction value, and calculates the removal ratio and the residual ratio of the residual liquid. Further, in a case where the correlation correction mode is set, the calibration processing unit 62 calculates a correlation correction value for correcting the correlations used to calculate the oxygen saturation levels in order to eliminate effects of the residual liquid. Note that the first image signal is an image signal that corresponds to a first wavelength range in which the light absorption amount changes in accordance with specific biological information that changes in accordance with the concentration of hemoglobin pigment, and the second image signal is an image signal that corresponds to a second wavelength range in which the light absorption amount changes in accordance with a factor other than the specific biological information that changes in accordance with the concentration of hemoglobin pigment.

The video signal generation unit 64 converts image data of the normal image from the normal image generation unit 58 or image data of the oxygen saturation image from the oxygen saturation image generation unit 60 to video signals that enable full-color display on the monitor 18. The video signals obtained as a result of conversion are input to the monitor 18. Accordingly, the normal image or the oxygen saturation image is displayed on the monitor 18. Further, when needed, the video signal generation unit 64 converts image data from the calibration processing unit 62 to video signals that enable full-color display on the monitor 18.

Figure 8:
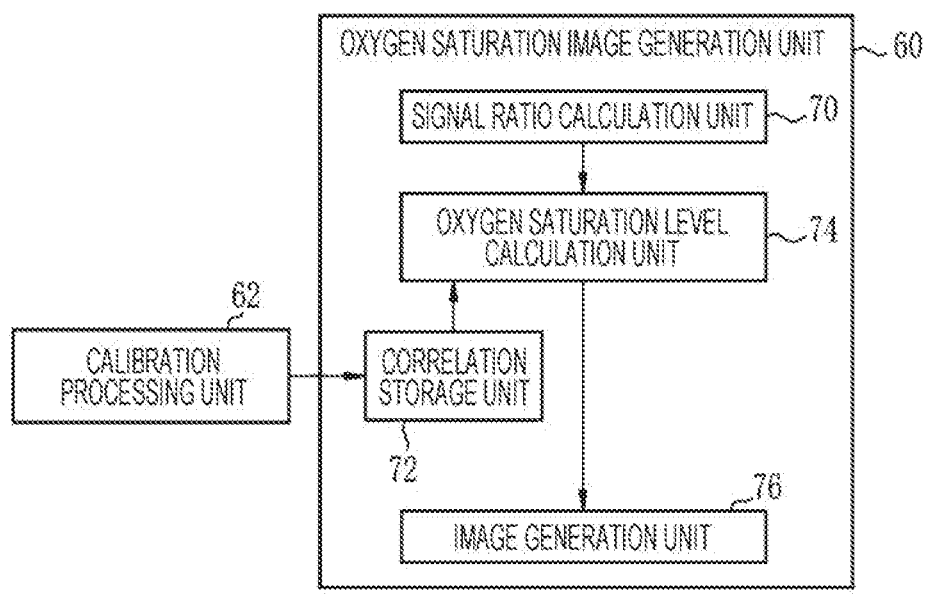
FIG. 8 is a block diagram illustrating functions of an oxygen saturation image generation unit.

As illustrated in FIG. 8, the oxygen saturation image generation unit 60 includes a signal ratio calculation unit 70, a correlation storage unit 72, an oxygen saturation level calculation unit 74, and an image generation unit 76. The signal ratio calculation unit 70 calculates signal ratios that are used by the oxygen saturation level calculation unit 74 to calculate oxygen saturation levels. Specifically, the signal ratio calculation unit 70 calculates, for each pixel, a signal ratio B1/G2 between the B1 image signal and the G2 image signal, a signal ratio R2/G2 between the R2 image signal and the G2 image signal, and a signal ratio G2/B2 between the G2 image signal and the B2 image signal.

Figure 9:
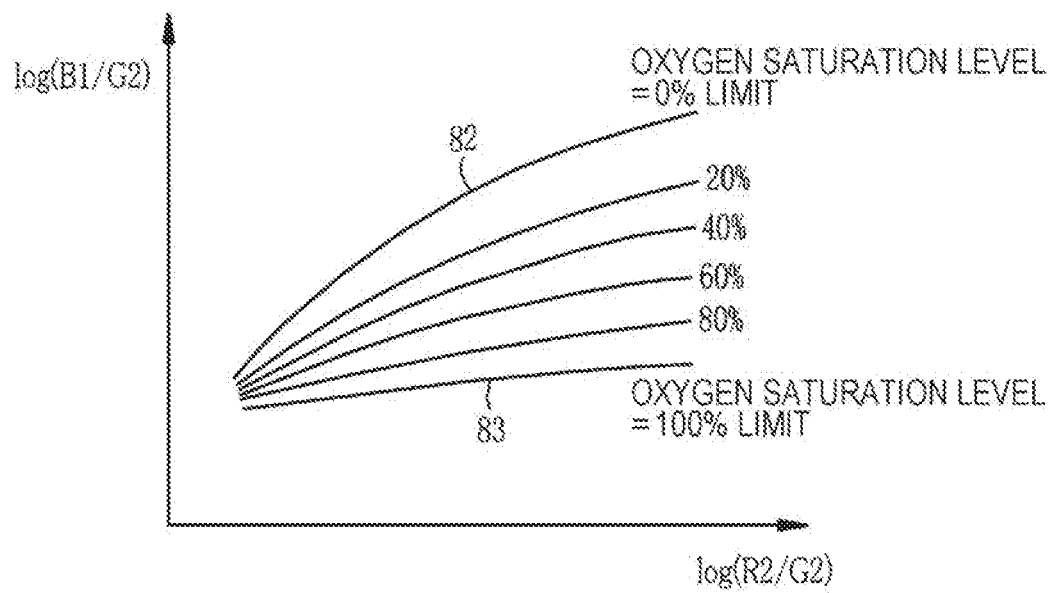
FIG. 9 is a graph illustrating the positions of isopleths of oxygen saturation levels in a first feature space, where the vertical axis represents log(B1/G2) and the horizontal axis represents log(R2/G2)

The correlation storage unit 72 stores correlations between the signal ratios calculated by the signal ratio calculation unit 70 and oxygen saturation levels in storage means, such as an LUT (Look-Up Table). In a case where the correlations are expressed in a first feature space defined by the vertical axis representing log(B1/G2) and the horizontal axis representing log(R2/G2), an isopleth that connects portions for which the oxygen saturation levels are the same is formed substantially in the horizontal axis direction in the first feature space, as illustrated in FIG. 9. Further, an isopleth for a larger oxygen saturation level is located on a lower side in the vertical axis direction. For example, the isopleth 83 for a 100% oxygen saturation level is located below the isopleth 82 for a 0% oxygen saturation level.

Note that the position and shape of each isopleth in the first feature space can be obtained in advance by a physical simulation of light scattering. Further, the correlation storage unit 72 stores the correlations between the signal ratios B1/G2 and R2/G2 and the oxygen saturation levels; however, the correlation storage unit 72 need not store the correlations with the signal ratios B1/G2 and R2/G2 and may store correlations between first arithmetic values obtained by performing a specific operation (for example, difference processing) based on the B1 image signals, the G2 image signals, and the R2 image signals and the oxygen saturation levels.

Figure 10:
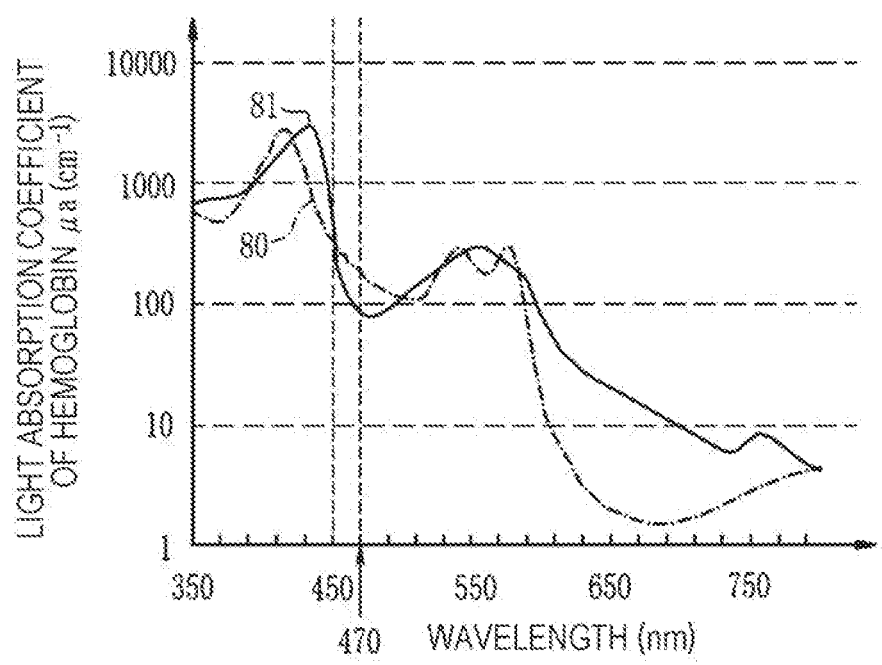
FIG. 10 is a graph illustrating the light absorption coefficient of oxyhemoglobin and that of reduced hemoglobin.

The above-described correlations are closely related to the light absorption characteristics and light scattering characteristics of oxyhemoglobin (graph 80) or reduced hemoglobin (graph 81) illustrated in FIG. 10 to each other. For example, in a wavelength range in which the difference in the light absorption coefficient between oxyhemoglobin and reduced hemoglobin is large, such as the wavelength range 470±10 nm of the second blue light BL, the light absorption amount changes in accordance with the oxygen saturation level of hemoglobin, and therefore, information regarding the oxygen saturation level can be easily handled. Therefore, when the signal ratio B1/G2 involving the B1 image signal corresponding to the second blue light BL having a center wavelength of 470 nm is used, the oxygen saturation level can be calculated. However, the signal ratio B1/G2 not only depends on the oxygen saturation level but also depends on the blood volume to a large degree. Therefore, in addition to the signal ratio B1/G2, the signal ratio R2/G2 that changes mainly in accordance with the blood volume is also used, so that the oxygen saturation level can be accurately obtained without being affected by the blood volume. Note that, in a wavelength range of 540±20 nm, which is the wavelength range of green light included in the G2 image signal, the light absorption coefficient of hemoglobin is relatively high, and therefore, the wavelength range of 540±20 nm is a wavelength range in which the light absorption amount is likely to change in accordance with the blood volume.

Figure 11:
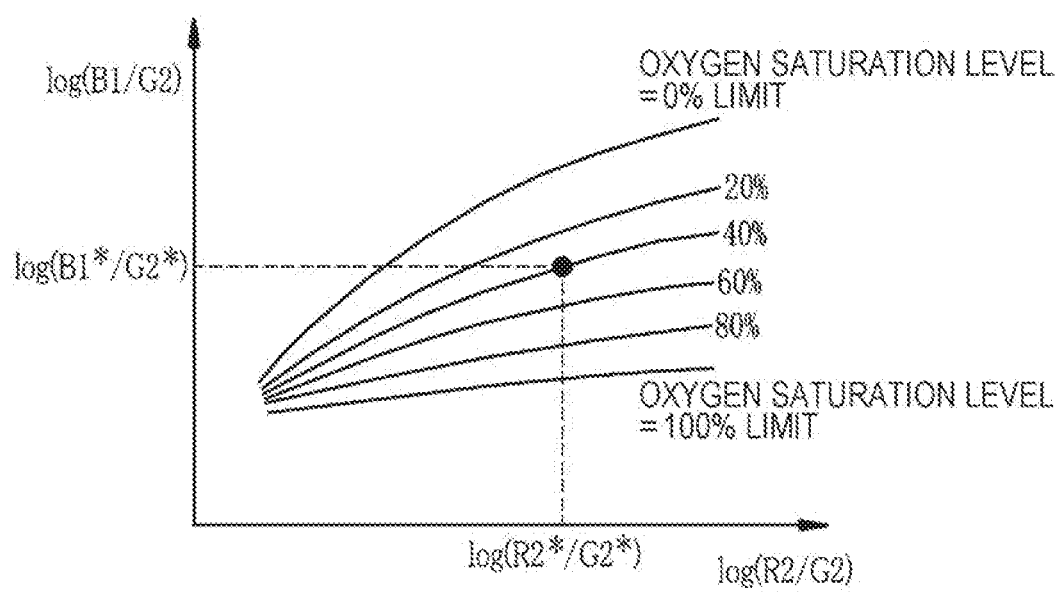
FIG. 11 is a diagram for explaining an oxygen saturation level calculation method.

The oxygen saturation level calculation unit 74 refers to the correlations stored in the correlation storage unit 72 and calculates an oxygen saturation level corresponding to the signal ratios B1/G2 and R2/G2 for each pixel. For example, in the case where the oxygen saturation level calculation unit 74 refers to the correlations stored in the correlation storage unit 72, an oxygen saturation level corresponding to the signal ratios B1*/G2* and R2*/G2* of a specific pixel is "40%", as illustrated in FIG. 11. Therefore, the oxygen saturation level calculation unit 74 calculates the oxygen saturation level as "40%".

Note that there is little chance that the signal ratios B1/G2 and R2/G2 become extremely large or extremely small. That is, there is little chance that the combinations of the values of the signal ratios B1/G2 and R2/G2 are distributed below the isopleth 83 (see FIG. 9) that corresponds to a 100% oxygen saturation level, which is the upper limit, or to the contrary, the combinations are distributed above the isopleth 82 (see FIG. 9) that corresponds to a 0% oxygen saturation level, which is the lower limit. However, in a case where the combinations are distributed below the isopleth 83 that corresponds to the upper limit, the oxygen saturation level is assumed to be 100%, and in a case where the combinations are distributed above the isopleth 82 that corresponds to the lower limit, the oxygen saturation level calculation unit 74 assumes the oxygen saturation level to be 0%. Further, in a case where a point that corresponds to the signal ratios B1/G2 and R2/G2 is not distributed between the isopleth 83 corresponding to the upper limit and the isopleth 82 corresponding to the lower limit, display may be performed so that the low reliability level of the oxygen saturation level at the pixel is known, or the oxygen saturation level need not be calculated.

The image generation unit 76 uses the oxygen saturation levels calculated by the oxygen saturation level calculation unit 74 to generate an oxygen saturation image, which is an image representing the oxygen saturation levels. Specifically, the image generation unit 76 obtains the B2 image signals, the G2 image signals, and the R2 image signals and applies, for each pixel, a gain corresponding to the oxygen saturation level to these image signals. The image generation unit 76 uses the B2 image signals, the G2 image signals, and the R2 image signals to which gains are applied to generate RGB image data. For example, for a pixel for which the oxygen saturation level is 60% or higher, the image generation unit 76 multiplies each of the B2 image signal, the G2 image signal, and the R2 image signal by the same gain "1". On the other hand, for a pixel for which the oxygen saturation level is lower than 60%, the image generation unit 76 multiplies the B2 image signal by a gain smaller than "1" and multiplies the G2 image signal and the R2 image signal by a gain equal to or larger than "1". The B2 image signals, the G2 image signals, and the R2 image signals after this gain processing are used to generate RGB image data, which corresponds to the oxygen saturation image.

In the oxygen saturation image generated by the image generation unit 76, a high-oxygen region (a region in which the oxygen saturation levels are from 60 to 100%) is represented in colors the same as those of a normal observation image. On the other hand, a low-oxygen region in which the oxygen saturation levels are below a specific value (a region in which the oxygen saturation levels are from 0 to 60%) is represented in colors (pseudo colors) that are different from those of a normal observation image.

Note that, in this embodiment, the image generation unit 76 performs multiplication by gains for representation in pseudo colors only for a low-oxygen region; however, the image generation unit 76 may apply gains corresponding to oxygen saturation levels also for a high-oxygen region to represent the entire oxygen saturation image in pseudo colors. Further, the low-oxygen region and the high-oxygen region are determined on the basis of an oxygen saturation level of 60%; however, this boundary may be set to any value.

Figure 12:
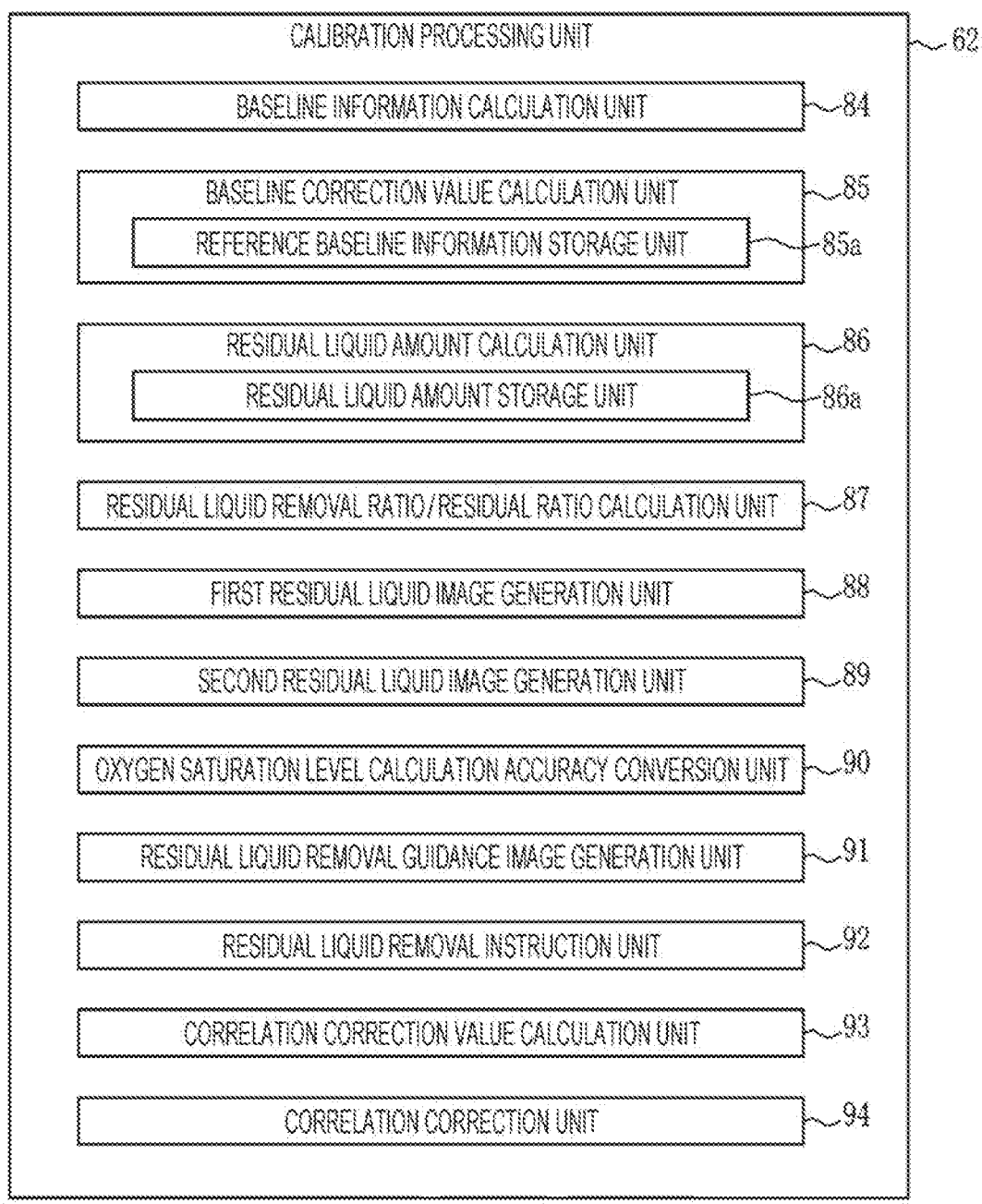
FIG. 12 is a block diagram illustrating functions of a calibration processing unit.

As illustrated in FIG. 12, the calibration processing unit 62 includes a baseline information calculation unit 84, a baseline correction value calculation unit 85, a residual liquid amount calculation unit 86, a residual liquid removal ratio/residual ratio calculation unit 87, a first residual liquid image generation unit 88, a second residual liquid image generation unit 89, an oxygen saturation level calculation accuracy conversion unit 90, a residual liquid removal guidance image generation unit 91, a residual liquid removal instruction unit 92, a correlation correction value calculation unit 93, and a correlation correction unit 94.

The baseline information calculation unit 84 calculates baseline information that includes information regarding a yellow pigment in the living body and that is not affected by the oxygen saturation level from the input Bp image signals, Bq image signals, Gr image signals, and Rs image signals. Specifically, the baseline information calculation unit 84 calculates a signal ratio Bp/Gr between the Bp image signal and the Gr image signal for each pixel, calculates a signal ratio Bq/Gr between the Bq image signal and the Gr image signal for each pixel, and calculates a signal ratio Rs/Gr between the Rs image signal and the Gr image signal for each pixel.

It is preferable that the baseline information have information regarding the light scattering characteristics or light absorption characteristics of the observation target in addition to information regarding a yellow pigment. Further, although the baseline information changes in accordance with the concentration of a yellow pigment, it is preferable that the baseline information change in accordance with the concentration of a pigment other than hemoglobin included in the observation target, in addition to a yellow pigment. It is preferable that the pigment other than hemoglobin is a pigment composition included in the living body or a pigment used at the time of endoscopic observation. Further, it is preferable that the pigment other than hemoglobin include at least any of a yellow pigment, such as bilirubin or stercobilin, a bluish violet series pigment, such as indigo carmine or crystal violet, a brown series pigment, such as Lugol, or a white pigment, such as acetic acid.

Figure 13:
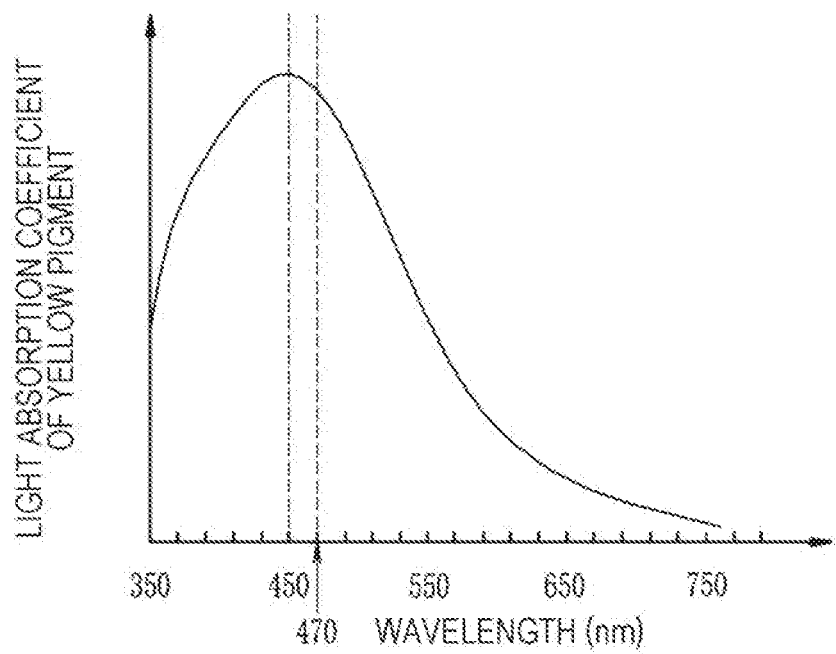
FIG. 13 is a graph illustrating the light absorption coefficient of a yellow pigment.

Here, Bp of the signal ratio Bp/Gr is an image signal that corresponds to the first blue light BS. The wavelength range 450±10 nm of the first blue light BS belongs to a blue-color range in which the light absorption coefficient of hemoglobin is relatively high, and includes an equal-absorption wavelength at which the light absorption coefficient of oxyhemoglobin and that of reduced hemoglobin are the same, as illustrated in FIG. 10. Further, the wavelength range 450±10 nm of the first blue light BS has an absorption peak wavelength at which the light absorption coefficient of a yellow pigment reaches a highest point as illustrated in FIG. 13, and therefore, is a wavelength range in which the light absorption amount is likely to change in accordance with the concentration of a yellow pigment. Therefore, the signal ratio Bp/Gr does not depend on the oxygen saturation level, but the signal values change in accordance with the concentration of a yellow pigment and the blood volume. Note that the wavelength range 540±20 nm of green light included in the Gr image signals is a wavelength range in which the light absorption amount is likely to change in accordance with the blood volume, as described above.

Bq of the signal ratio Bq/Gr is an image signal that corresponds to the second blue light BL. The wavelength range 470±10 nm of the second blue light BL belongs to a blue-color range in which the light absorption coefficient of hemoglobin is relatively high as described above and includes a different-absorption wavelength at which the light absorption coefficient of oxyhemoglobin and that of reduced hemoglobin are different (see FIG. 10), and therefore, is a wavelength range in which the light absorption amount is likely to change in accordance with the oxygen saturation level of hemoglobin. Further, the center wavelength 470 nm of the second blue light BL has an absorption coefficient slightly lower than that at the absorption peak wavelength for a yellow pigment and higher than that in the other wavelength range (see FIG. 13). Therefore, regarding the signal ratio Bq/Gr, the signal values change in accordance with the oxygen saturation level, the concentration of a yellow pigment, and the blood volume. On the other hand, regarding the signal ratio Rs/Gr, the signal values change little regardless of the oxygen saturation level and the concentration of a yellow pigment and change in accordance with the blood volume.

The baseline information calculation unit 84 adjusts $\phi$ so that a second arithmetic value obtained as a result of a correction operation based on the following expression (expression A) remains constant even if the oxygen saturation level changes. Information formed of the second arithmetic value after adjustment of $\phi$ and the signal ratio Rs/Gr is assumed to be baseline information. The baseline information is information that changes in accordance with the concentration of a yellow pigment and information that does not depend on the oxygen saturation level. Here, "does not depend" means that at least the baseline information changes to a larger degree in accordance with the concentration of a yellow pigment than the oxygen saturation level.

Second arithmetic value=Signal ratio $Bp/Gr \times \cos \phi$–Signal ratio $Bq/Gr \times \sin \phi$    (Expression A)

Note that the phase $\phi$ in (expression A) is determined so as not to depend on the oxygen saturation level. Similarly, when the phase $\phi$ is determined so as not to depend on specific biological information that changes in accordance with the concentration of hemoglobin pigment included in the observation target, such as the blood vessel density or blood vessel depth, the blood vessel thickness, or the blood concentration, "baseline information" that does not depend on such specific biological information can be determined.

The baseline correction value calculation unit 85 calculates a baseline correction value $\Delta Z$ on the basis of predetermined reference baseline information and the baseline information calculated by the baseline information calculation unit 84. The reference baseline information is stored in a reference baseline information storage unit 85a. The reference baseline information is a reference for evaluating baseline information, is obtained in a state where a yellow pigment does not exist, and is determined as information that does not depend on the oxygen saturation level. Specifically, the reference baseline information is obtained by adjusting $\phi$ in a state where effects of a yellow pigment are eliminated (that is, in a state where a yellow pigment does not exist) so that the second arithmetic value (=Signal ratio Bp/Gr×cos $\phi$–Signal ratio Bq/Gr×sin $\phi$) based on (expression A) above remains constant even if the oxygen saturation level changes. Information formed of the second arithmetic value after adjustment of $\phi$ and the signal ratio Rs/Gr is assumed to be the reference baseline information.

Figure 14:
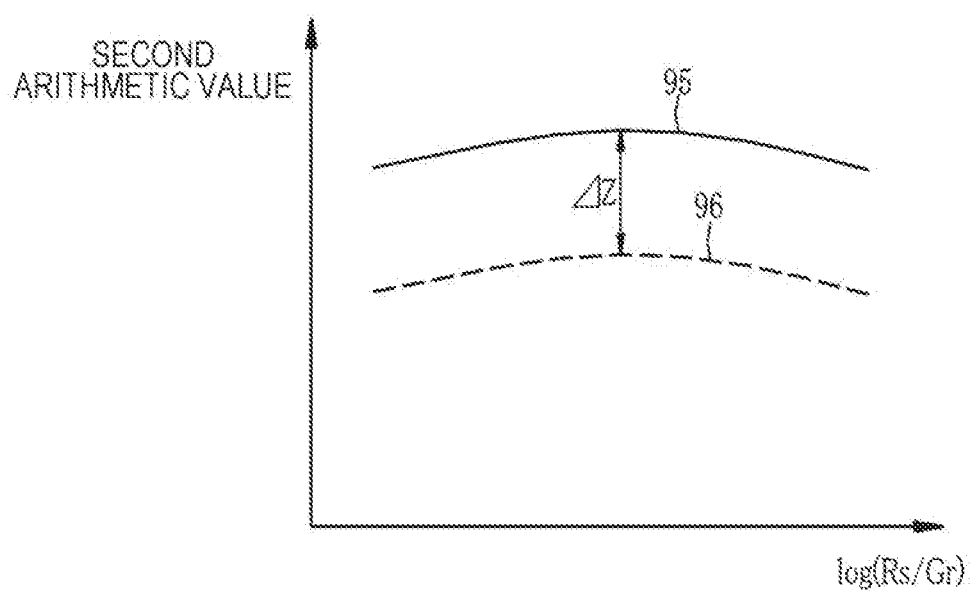
FIG. 14 is a graph illustrating the positions of a reference line and an actual measurement line in a second feature space, where the vertical axis represents a second arithmetic value and the horizontal axis represents log(Rs/Gr)

The method for calculating the baseline correction value $\Delta Z$ by the baseline correction value calculation unit 85 is described below with reference to a second feature space illustrated in FIG. 14. This second feature space is formed on the basis of the vertical axis that represents the second arithmetic value (=Signal ratio Bp/Gr×cos $\phi$– Signal ratio Bq/Gr×sin $\phi$) based on (expression A) and the horizontal axis that represents log(Rs/Gr). In a case where reference baseline information and baseline information are expressed in the second feature space, the reference line 95 that represents the distribution of reference baseline information not affected by a yellow pigment and the actual measurement line 96 along which baseline information affected by a yellow pigment is distributed are formed substantially in the horizontal axis direction, as illustrated in FIG. 14. The actual measurement line 96 is an equal-concentration line on which the concentrations of a yellow pigment are the same. Further, in the second feature space, the reference line 95 is located above the actual measurement line 96. In the second feature space, as effects of a yellow pigment increase, the actual measurement line 96 is located at a lower position, and the difference between the reference line 95 and the actual measurement line 96 increases.

The baseline correction value calculation unit 85 calculates the difference between the reference line 95 and the actual measurement line 96 as the baseline correction value ΔZ. The baseline correction value ΔZ is a correction value for adjusting the baseline information represented by the actual measurement line 96 to the reference baseline information represented by the reference line 95. The baseline correction value ΔZ is used not only in calculation of the residual liquid amount but also in correction of the correlations that are used to calculate oxygen saturation levels. Note that the baseline correction value ΔZ may be calculated by performing a conversion process that is a combination of matrix processing and a 1D-LUT (1-Dimensional Look-Up Table) for the Bp image signal, the Bq image signal, the Gr image signal, and the Rs image signal.

Figure 15:
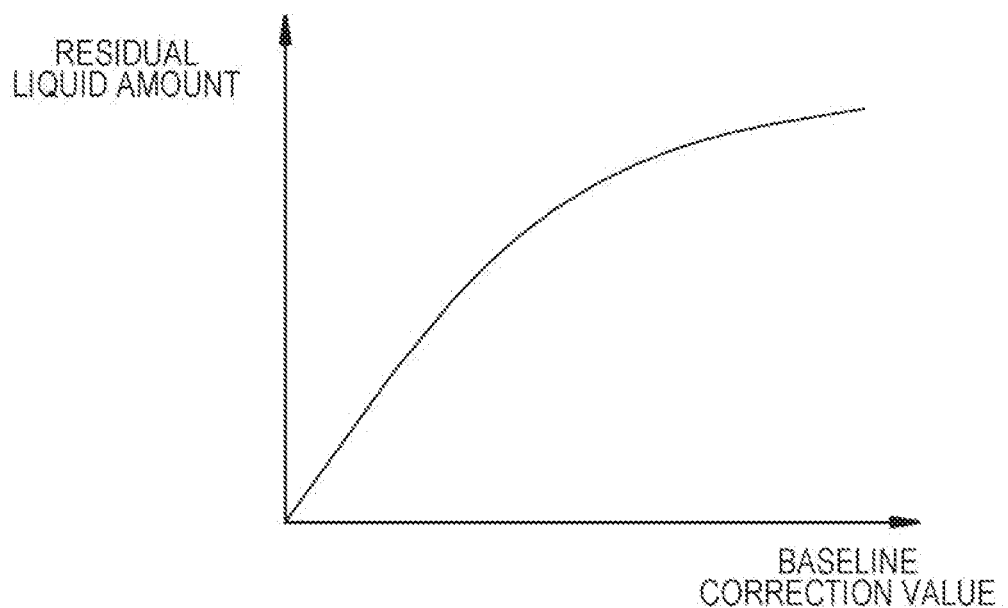
FIG. 15 is a graph illustrating a relationship between a baseline correction value and a residual liquid amount.
Figure 16:
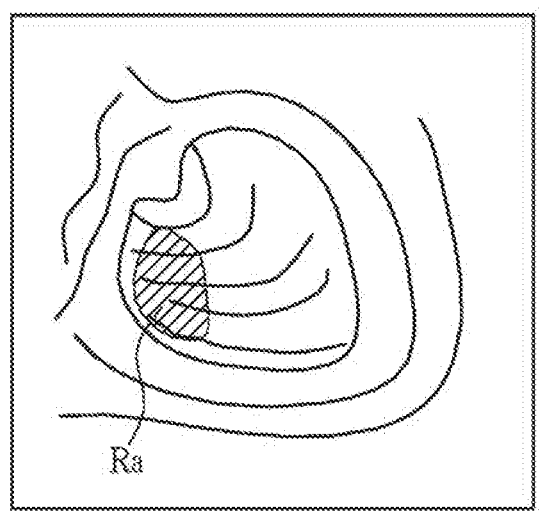
FIG. 16 illustrates an image indicating a residual liquid region Ra in an observation target.

The residual liquid amount calculation unit 86 calculates the residual liquid amount of a residual liquid included in the observation target. The residual liquid amount of a residual liquid that includes a yellow pigment increases as the baseline correction value ΔZ increases, as illustrated in FIG. 15, and therefore, the residual liquid amount can be estimated from the baseline correction value ΔZ. The relationship between the residual liquid amount and the baseline correction value ΔZ is stored in a residual liquid amount storage unit 86a. The residual liquid amount calculation unit 86 refers to the residual liquid amount storage unit 86a (for example, an LUT (Look-Up Table)) and calculates the residual liquid amount from the baseline correction value ΔZ. Further, when the baseline correction value ΔZ is calculated for each pixel, the residual liquid amount can be calculated for each pixel. For example, the residual liquid amount calculation unit 86 may determine a pixel region in which the residual liquid amounts are within a specific range to be a residual liquid region in which a residual liquid exists, and this residual liquid region, which is a residual liquid region Ra, may be highlighted and displayed in a specific color, etc., as illustrated in FIG. 16.

The residual liquid removal ratio/residual ratio calculation unit 87 calculates a pre-residual-liquid-removal residual liquid amount that is a residual liquid amount before removal of a residual liquid by the residual liquid removal part 6 and a post-residual-liquid-removal residual liquid amount that is a residual liquid amount after removal of the residual liquid, and calculates the removal ratio of the residual liquid from the pre-residual-liquid-removal residual liquid amount and the post-residual-liquid-removal residual liquid amount. Further, the residual liquid removal ratio/residual ratio calculation unit 87 calculates the residual ratio of the residual liquid from the pre-residual-liquid-removal residual liquid amount and the post-residual-liquid-removal residual liquid amount. To calculate the removal ratio and the residual ratio of a residual liquid, when removal of the residual liquid by the residual liquid removal part 6 is started, the residual liquid removal ratio/residual ratio calculation unit 87 calculates the residual liquid amount of the residual liquid calculated by the residual liquid amount calculation unit 86 immediately before removal of the residual liquid as the pre-residual-liquid-removal residual liquid amount. When removal of the residual liquid by the residual liquid removal part 6 is completed, the residual liquid removal ratio/residual ratio calculation unit 87 calculates the residual liquid amount of the residual liquid calculated by the residual liquid amount calculation unit 86 at that time point as the post-residual-liquid-removal residual liquid amount.

Here, it is preferable that removal of a residual liquid is started at the timing when either the air/water supply button 12h or the suction button 12i is operated. Further, regarding completion of removal of a residual liquid, it is preferable that removal of the residual liquid is assumed to be completed at the time point when a specific residual liquid removal completion condition that, for example, an operation of the air/water supply button 12h or the suction button 12i has been performed, and thereafter, the operation is not performed for a certain period is satisfied, or it is preferable that removal of the residual liquid is assumed to be completed in a case where a residual liquid removal completion instruction is given from the console 19, etc.

Figure 17:
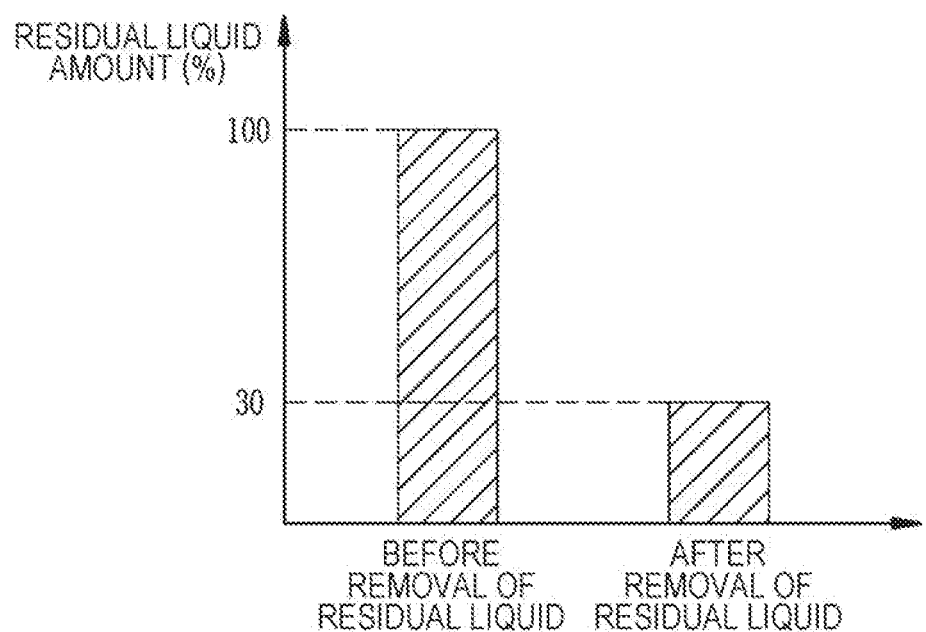
FIG. 17 is a column chart illustrating a pre-residual-liquid-removal residual liquid amount and a post-residual-liquid-removal residual liquid amount.

Specifically, the residual liquid removal ratio/residual ratio calculation unit 87 calculates the ratio of the post-residual-liquid-removal residual liquid amount to the pre-residual-liquid-removal residual liquid amount as the residual liquid residual ratio. Further, the residual liquid removal ratio/residual ratio calculation unit 87 calculates the decrease amount of the residual liquid by subtracting the post-residual-liquid-removal residual liquid amount from the pre-residual-liquid-removal residual liquid amount and calculates the ratio of the decrease amount of the residual liquid to the pre-residual-liquid-removal residual liquid amount as the residual liquid removal ratio. For example, in a case where the pre-residual-liquid-removal residual liquid amount is 100% and the post-residual-liquid-removal residual liquid amount is 30%, the residual liquid removal ratio is 70% ((100−30)/100×100%) (see FIG. 17). Note that the residual liquid residual ratio and the residual liquid removal ratio are calculated from the pre-residual-liquid-removal residual liquid amount and the post-residual-liquid-removal residual liquid amount and may be calculated from a baseline correction value obtained at the time when residual liquid removal is started and a baseline correction value obtained at the time when residual liquid removal is completed.

Figure 18:
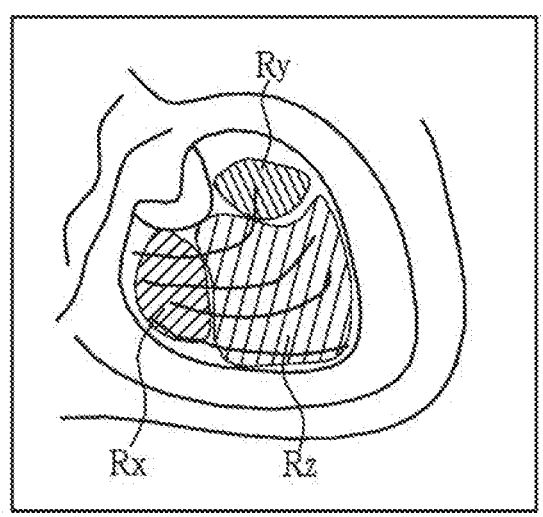
FIG. 18 illustrates a first residual liquid image.

The first residual liquid image generation unit 88 generates a first residual liquid image that represents the distribution of the removal ratio of the residual liquid calculated by the residual liquid removal ratio/residual ratio calculation unit 87. The generated first residual liquid image is displayed on the monitor 18. The first residual liquid image generation unit 88 generates the first residual liquid image represented by using different colors in accordance with the removal ratio of the residual liquid. For example, it is preferable that, in the first residual liquid image, a low-removal-ratio region Rx in which the removal ratio is low is displayed in a first color (for example, red), a medium-removal-ratio region Ry in which the removal ratio is medium is displayed in a second color (for example, green), and a high-removal-ratio region Rz in which the removal ratio is high is displayed in a third color (for example, white that is substantially transparent), as illustrated in FIG. 18.

Accordingly, when display is performed in different colors in accordance with the removal ratio of the residual liquid, the visibility of a portion from which the residual liquid is not satisfactorily removed can be increased. Consequently, the portion from which the residual liquid is to be further removed is identified, and therefore, unsatisfactory residual liquid removal or unnecessary removal can be prevented, and residual liquid removal can be efficiently performed. Further, color display in accordance with the removal ratio of the residual liquid is performed for each pixel, and therefore, the existence of the residual liquid that is difficult to check on an observation image can be recognized, and the residual liquid can be removed. Note that the first residual liquid image generation unit 88 may generate the first residual liquid image that represents not only the distribution of the removal ratio of the residual liquid but also the distribution of residual liquid information regarding the residual liquid included in the observation target, such as the residual ratio of the residual liquid and the residual liquid amount.

Figure 19:
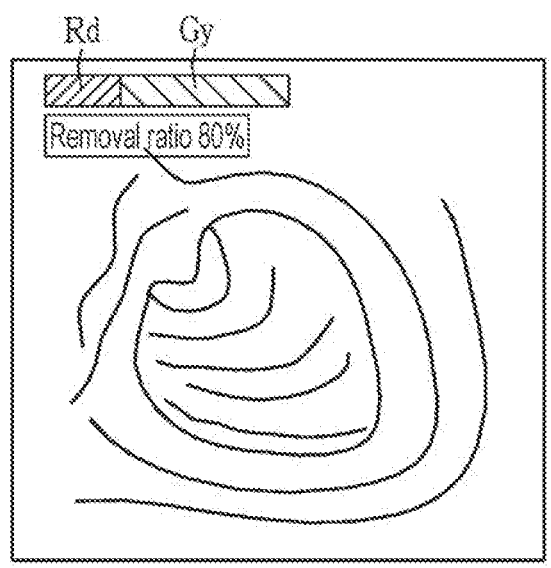
FIG. 19 illustrates a second residual liquid image.

The second residual liquid image generation unit 89 generates a second residual liquid image that includes an image of the observation target and the removal ratio of the residual liquid calculated by the residual liquid removal ratio/residual ratio calculation unit 87, the removal ratio being indicated by a numerical value or an indicator. The generated second residual liquid image is displayed on the monitor 18. Regarding the second residual liquid image, as illustrated in FIG. 19, together with an image of the observation target, the removal ratio (80%) of the residual liquid is displayed by a numerical value and is also displayed by an indicator in which the residual ratio of the residual liquid is represented in red Rd and the removal ratio of the residual liquid is indicated by Gy. Note that the second residual liquid image generation unit 89 may generate the second residual liquid image on which residual liquid information, such as the residual ratio of the residual liquid and the residual liquid amount, is displayed by a numerical value or an indicator in addition to the removal ratio of the residual liquid. An image, that is, either the first residual liquid image or the second residual liquid image, to be displayed on the monitor 18 is set on the console 19.

Figure 20:
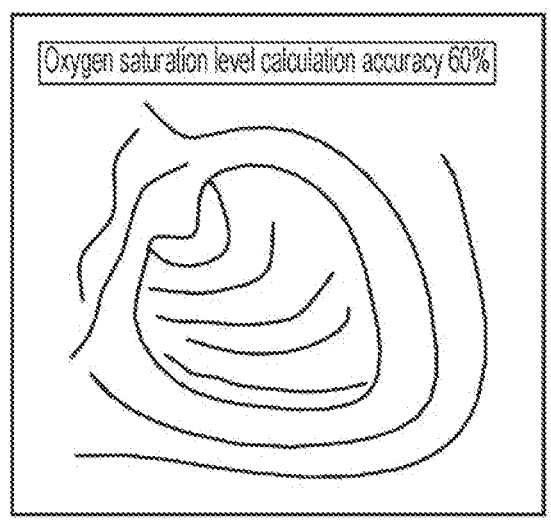
FIG. 20 illustrates an image indicating an oxygen saturation level calculation accuracy.

The oxygen saturation level calculation accuracy conversion unit 90 (biological information calculation accuracy conversion unit) converts the residual ratio of a residual liquid to the calculation accuracy of an oxygen saturation level that is calculated by the oxygen saturation level calculation unit 74 (biological information calculation unit). As the residual ratio of a residual liquid increases, the calculation accuracy of the oxygen saturation level decreases, and therefore, conversion from the residual ratio of a residual liquid to the calculation accuracy of the oxygen saturation level is possible. For example, in a case where the residual ratio of a residual liquid is "0%", the calculation accuracy of the oxygen saturation level is assumed to be "100%", and conversion is performed in such a manner that the calculation accuracy of the oxygen saturation level decreases as the residual ratio of a residual liquid increases. The calculation accuracy of the oxygen saturation level obtained as a result of conversion is displayed on the monitor 18 as illustrated in FIG. 20 (in FIG. 20, the calculation accuracy of the oxygen saturation level is displayed as "60%").

Note that the removal ratio of a residual liquid may be converted to the calculation accuracy of the oxygen saturation level. In this case, as the removal ratio of the residual liquid increases, the calculation accuracy of the oxygen saturation level increases. Further, the residual liquid amount may be converted to the calculation accuracy of the oxygen saturation level. In this case, as in the case of the residual ratio, as the residual liquid amount increases, the calculation accuracy of the oxygen saturation level decreases. Further, in addition to conversion of the residual ratio, etc. to the calculation accuracy of the oxygen saturation level, in a case where the biological information calculation unit calculates specific biological information, such as the blood vessel density, other than the oxygen saturation level, residual liquid information, such as the residual ratio, the removal ratio, the residual liquid amount, etc. of the residual liquid, may be converted to the calculation accuracy of the specific biological information.

Figure 21:
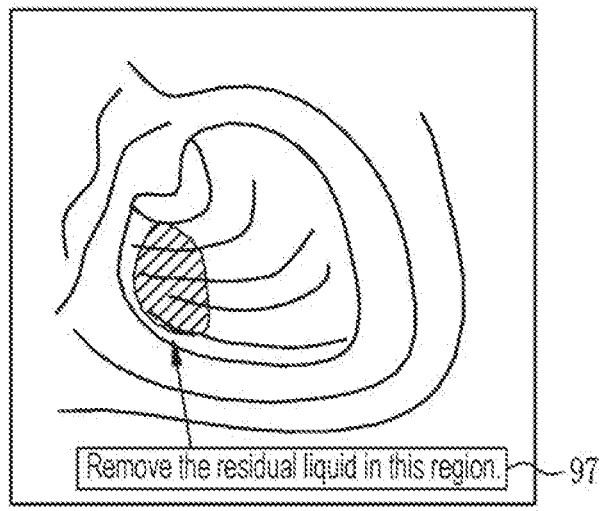
FIG. 21 illustrates a residual liquid removal guidance image.

The residual liquid removal guidance image generation unit 91 generates a residual liquid removal guidance image for urging the user to remove a residual liquid on the observation target by using the residual liquid removal part 6 when the removal ratio or the residual ratio of the residual liquid satisfies a specific condition. The generated residual liquid removal guidance image is displayed on the monitor 18. On the residual liquid removal guidance image, as illustrated in FIG. 21, for example, a low-removal-ratio region in which the removal ratio of the residual liquid is low is displayed in a first color (for example, red), and guidance 97 for urging removal of the residual liquid in the low-removal-ratio region by, for example, jetting of air or water or suction is also displayed. At this time, it is preferable to also display a target removal ratio. Note that, also in a case where residual liquid information, such as the residual liquid amount, other than the removal ratio or the residual ratio of the residual liquid satisfies a specific condition, the residual liquid removal guidance image generation unit 91 may generate and display, on the monitor 18, the residual liquid removal guidance image.

The residual liquid removal instruction unit 92 automatically instructs the residual liquid removal part 6 to remove a residual liquid on the observation target when the removal ratio or the residual ratio of the residual liquid satisfies a specific condition. For example, a target removal ratio is determined in advance, and the residual liquid removal instruction unit 92 automatically detects whether a region in which the removal ratio is below the target removal ratio exists. In a case where a region in which the removal ratio is below the target removal ratio is detected, for example, jetting of air or water or suction is automatically performed for the detected region to remove the residual liquid. Note that also in a case where residual liquid information, such as the residual liquid amount, other than the removal ratio or the residual ratio of the residual liquid satisfies a specific condition, the residual liquid removal instruction unit 92 may automatically instruct the residual liquid removal part 6 to remove the residual liquid.

Figure 22:
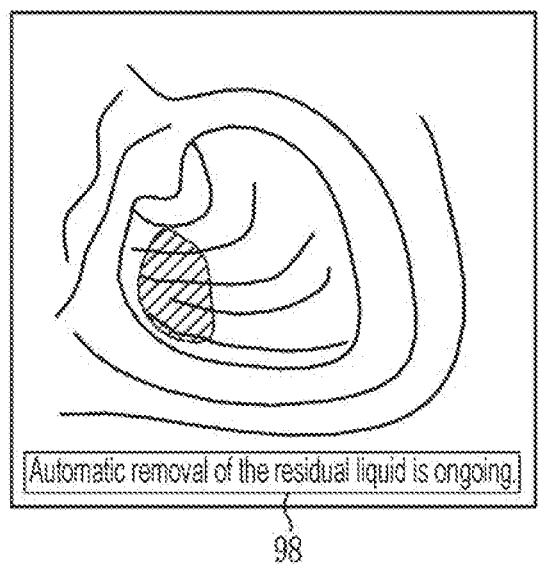
FIG. 22 illustrates an image in which a message stating that automatic removal is ongoing is displayed.

In this case, it is preferable that the removal ratio of the residual liquid in the detected region is monitored during residual liquid removal and that jetting of air or water or suction is automatically stopped when the removal ratio reaches the target removal ratio. Further it is preferable that residual liquid removal conditions, such as the amount of air to be supplied, the amount of water to be supplied, and the amount of suction, are set in accordance with residual liquid information, such as the removal ratio or the residual ratio of the residual liquid or the residual liquid amount. For example, in a case where the removal ratio of the residual liquid is low and is different from the target removal ratio to a large degree, it is preferable to set the amount of air to be supplied, the amount of water to be supplied, and the amount of suction among the residual liquid removal conditions to large values. Note that, in a case of automatically performing residual liquid removal, it is preferable to display a message 98 indicating that automatic removal is ongoing, as illustrated in FIG. 22.

The correlation correction value calculation unit 93 multiplies the baseline correction value $\Delta Z$ by a coefficient $\alpha$ to calculate a correlation correction value $\Delta D$ for correcting the correlations stored in the correlation storage unit 72 (Baseline correction value $\Delta Z \times$ Coefficient $\alpha$). The correlation correction unit 94 corrects the correlations stored in the correlation storage unit 72 on the basis of the correlation correction value $\Delta D$ calculated by the correlation correction value calculation unit 93. Specifically, in the first feature space (see FIG. 9), the correlation correction value $\Delta D$ is added to a value of $\log(B1/G2)$ on the vertical axis. Accordingly, in the first feature space, an isopleth that connects portions in which the oxygen saturation levels are the same moves in the direction of the vertical axis log(B1/G2). When an oxygen saturation level is calculated by using the correlations after this correction, even in a situation where effects of a yellow pigment exist on the observation target as well as in a case of a different body part or a different patient, the oxygen saturation level can be accurately calculated.

Figure 23:
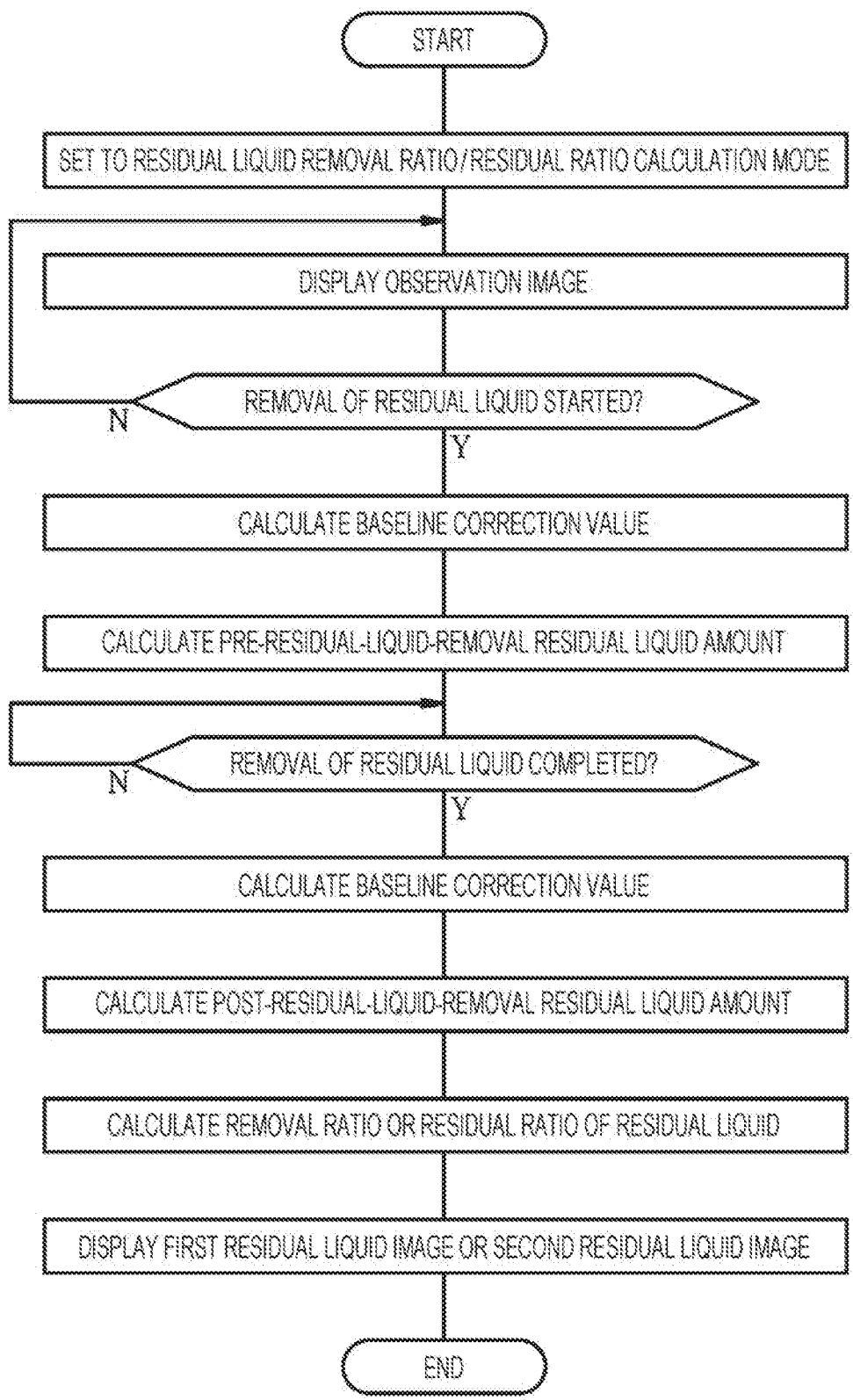
FIG. 23 is a flowchart illustrating a flow in a residual liquid removal ratio/residual ratio calculation mode.

Now, a flow of a process in the residual liquid removal ratio/residual ratio calculation mode in the calibration mode is described with reference to the flowchart illustrated in FIG. 23. When the mode switching SW 12*f* is used to switch to the residual liquid removal ratio/residual ratio calculation mode, the LEDs 20*a* to 20*d* are sequentially turned on, and the first blue light BS, the second blue light BL, the green light G, and the red light R are sequentially emitted. These light rays of four colors are radiated onto an observation target, and image capturing of the observation target is performed by the image sensor 44. The image sensor 44 outputs image signals based on which an image of the observation target is displayed on the monitor 18.

In response to the user operating the air/water supply button 12*h* or the suction button 12*i*, removal of a residual liquid by the residual liquid removal part 6 is started. At this time, from baseline information obtained immediately before the start of removal of the residual liquid and predetermined reference baseline information, a baseline correction value is calculated. From the calculated baseline correction value, the pre-residual-liquid-removal residual liquid amount is calculated. The calculated pre-residual-liquid-removal residual liquid amount is stored in a predetermined storage unit (not illustrated) in the processor device 16.

When removal of the residual liquid is completed, from baseline information obtained at the time point of completion of removal of the residual liquid and the predetermined reference baseline information, a baseline correction value is calculated. From the calculated baseline correction value, the post-residual-liquid-removal residual liquid amount is calculated. From the pre-residual-liquid-removal residual liquid amount and the post-residual-liquid-removal residual liquid amount, the removal ratio or the residual ratio of the residual liquid is calculated. On the basis of the calculated removal ratio or residual ratio of the residual liquid, a first residual liquid image representing the distribution of the removal ratio or residual ratio of the residual liquid is displayed on the monitor 18. Alternatively, a second residual liquid image that represents the removal ratio or residual ratio of the residual liquid by a numerical value or an indicator is displayed.

In this embodiment, a processing unit that performs various processes is implemented as any of the processors of various types as listed below in terms of hardware structure. The processors include a CPU (Central Processing Unit) that is a general-purpose processor executing software (program) to function as various processing units, a programmable logic device (PLD), such as an FPGA (Field-Programmable Gate Array), that is a processor for which the circuit configuration can be changed after manufacturing, and a dedicated electric circuit, such as an ASIC (Application-Specific Integrated Circuit), having a circuit configuration that is designed only for performing a specific process.

One processing unit may be constituted by one of the above-described processors or may be constituted by two or more processors of the same type or different types (for example, a plurality of FPGAs or a combination of a CPU and an FPGA). Further, a plurality of processing units may be constituted by one processor.

Further, more specifically, the above-described processors are implemented as electric circuits (circuitry) obtained by combining circuit elements, such as semiconductor elements, in terms of hardware structure.

Second Embodiment

In a second embodiment, instead of the LEDs 20*a* to 20*d* of four colors described in the first embodiment above, a broadband light source, such as a xenon lamp, and a rotating filter are used to illuminate an observation target. Further, instead of the image sensor 44, which is a color image sensor, a monochrome image sensor is used to capture images of an observation target. The other configuration is the same as that in the first embodiment.

Figure 24:
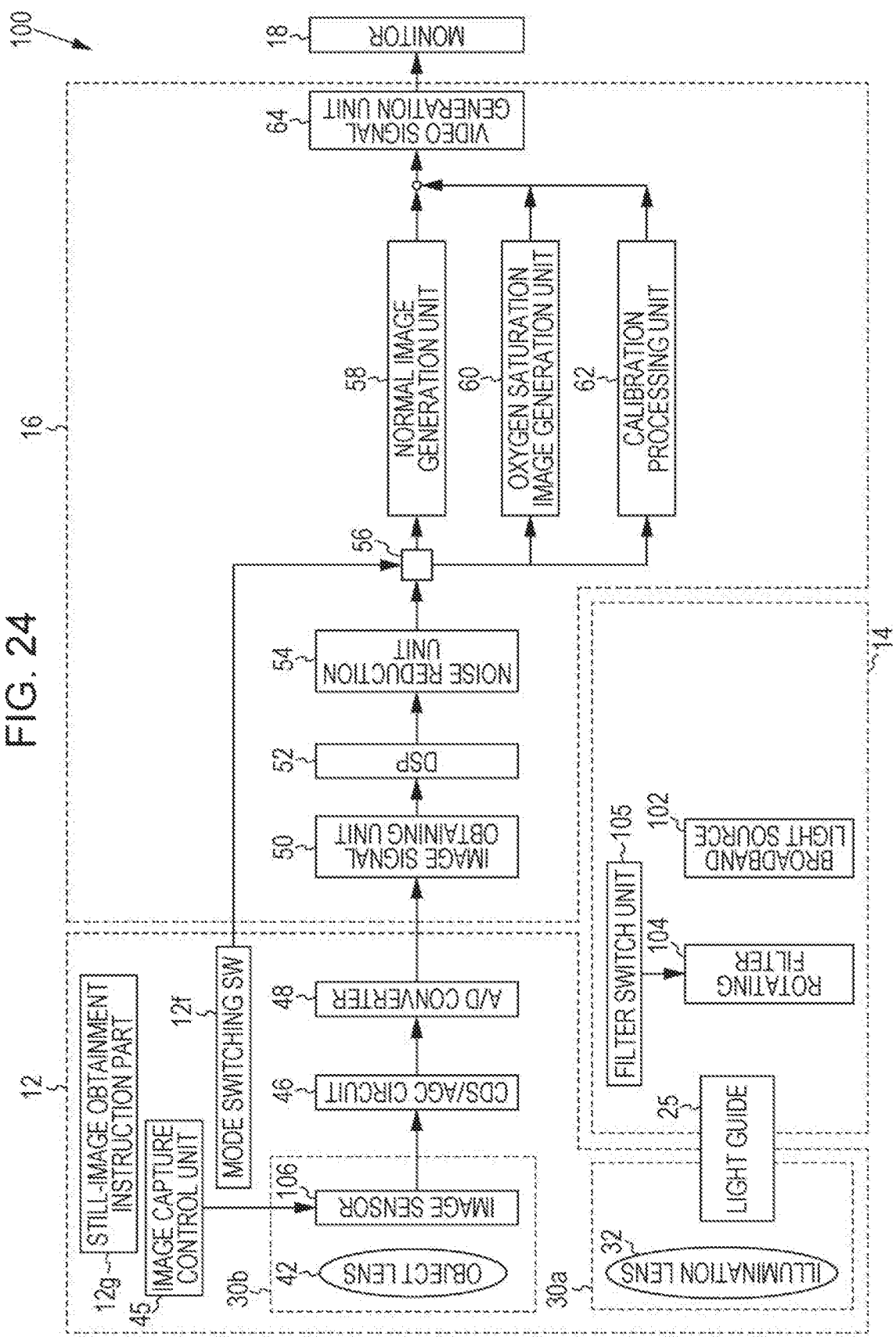
FIG. 24 is a block diagram illustrating functions of an endoscope system according to a second embodiment.

As illustrated in FIG. 24, in an endoscope system 100 according to the second embodiment, the light source device 14 is provided with a broadband light source 102, a rotating filter 104, and a filter switch unit 105 instead of the LEDs 20*a* to 20*d* of four colors. Further, the image capture optical system 30*b* is provided with a monochrome image sensor 106, in which color filters are not provided, instead of the image sensor 44, which is a color image sensor.

The broadband light source 102 is, for example, a xenon lamp or a white LED and emits white light in a wavelength range extending from blue to red. The rotating filter 104 includes an inner filter 108 provided close to the center and an outer filter 109 provided further from the center (see FIG. 25). The filter switch unit 105 is a unit for moving the rotating filter 104 in the radial direction. When the normal mode is set by the mode switching SW 12*f*, the inner filter 108 of the rotating filter 104 is inserted in the optical path of white light. When the oxygen saturation mode or the calibration mode is set, the outer filter 109 of the rotating filter 104 is inserted in the optical path of white light.

Figure 25:
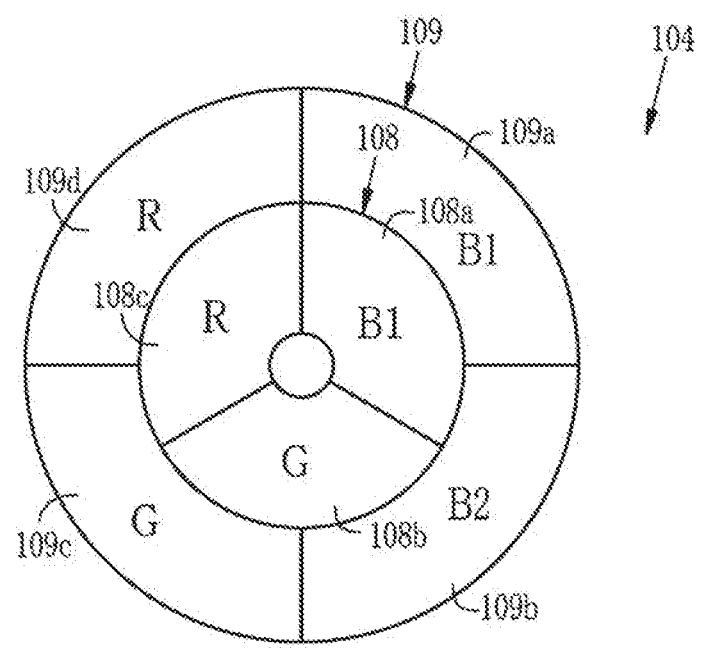
FIG. 25 is a plan view of a rotating filter.

As illustrated in FIG. 25, the inner filter 108 is provided with a B1 filter 108*a* that allows the first blue light BS in white light to pass therethrough, a G filter 108*b* that allows the green light G in the white light to pass therethrough, and an R filter 108*c* that allows the red light R in the white light to pass therethrough, in the circumferential direction. Therefore, in the normal mode, the rotating filter 104 rotates so that the first blue light BS, the green light G, and the red light R are sequentially radiated onto an observation target.

The outer filter 109 is provided with a B1 filter 109*a* that allows the first blue light BS in white light to pass therethrough, a B2 filter 109*b* that allows the second blue light BL in the white light to pass therethrough, a G filter 109*c* that allows the green light G in the white light to pass therethrough, and an R filter 109*d* that allows the red light R in the white light to pass therethrough, in the circumferential direction. Therefore, in the oxygen saturation mode and the calibration mode, the rotating filter 104 rotates so that the first blue light BS, the second blue light BL, the green light G, and the red light R are sequentially radiated onto an observation target.

In the endoscope system 100, in the normal mode, each time an observation target is illuminated with the first blue light BS, the green light G, or the red light R, image capturing of the observation target is performed with the monochrome image sensor 106. Accordingly, Bc image signals, Gc image signals, and Rc image signals are obtained. On the basis of these image signals of three colors, a normal image is generated with a method similar to that in the first embodiment described above.

On the other hand, in the oxygen saturation mode, each time an observation target is illuminated with the first blue light BS, the second blue light BL, the green light G, or the red light R, image capturing of the observation target is performed with the monochrome image sensor 106. Accordingly, B2 image signals, B1 image signals, G2 image signals, and R2 image signals are obtained. On the basis of these image signals of four colors, an oxygen saturation image is generated with a method similar to that in the first embodiment. Further, in the calibration mode, Bp image signals, Bq image signals, Gr image signals, and Rs image signals are obtained. On the basis of these image signals of four colors, the residual liquid amount is calculated or the correlations are corrected with a method similar to that in the first embodiment.

Third Embodiment

In a third embodiment, instead of the LEDs 20a to 20d of four colors described in the first embodiment above, a laser light source and a fluorescent body are used to illuminate an observation target. A description of part different from that in the first embodiment is given below, and a description of part substantially the same as that in the first embodiment is omitted.

Figure 26:
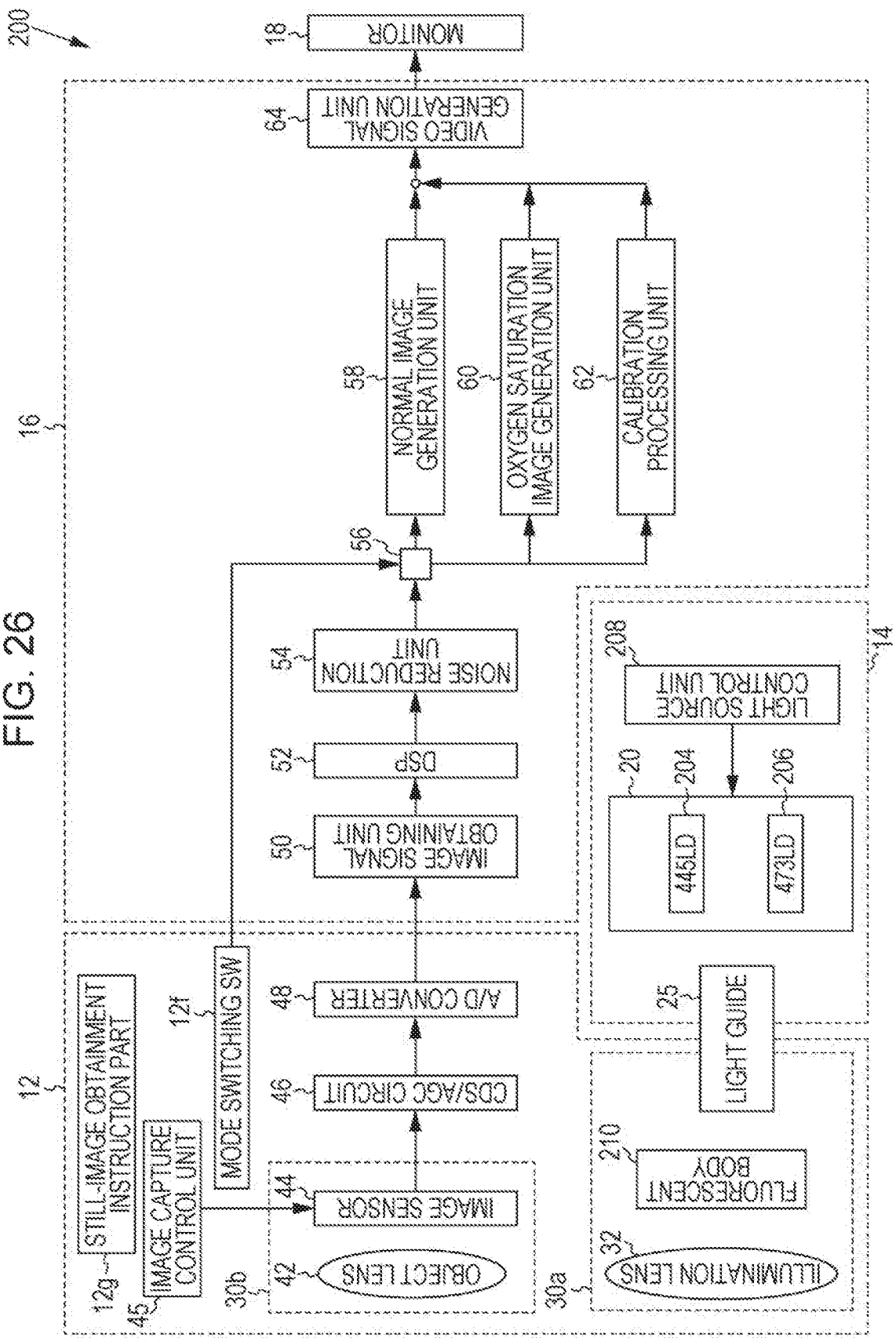
FIG. 26 is a block diagram illustrating functions of an endoscope system according to a third embodiment.

As illustrated in FIG. 26, in an endoscope system 200 according to a third embodiment, the light source 20 of the light source device 14 is provided with a blue laser light source (represented as "445LD" where LD represents "Laser Diode") 204 that emits blue laser light having a center wavelength of 445±10 nm and a blue-green laser light source (represented as "473LD") 206 that emits blue-green laser light having a center wavelength of 473±10 nm instead of the LEDs 20a to 20d of four colors. Light emission from a semiconductor light emitting element of each of the light sources 204 and 206 is individually controlled by a light source control unit 208.

In the normal mode, the light source control unit 208 turns on the blue laser light source 204. On the other hand, in the oxygen saturation mode and the calibration mode, the light source control unit 208 turns on the blue laser light source 204 and the blue-green laser light source 206 alternately.

Note that it is preferable to set the half-width of the blue laser light or the blue-green laser light to about ±10 nm. Further, as the blue laser light source 204 and the blue-green laser light source 206, a broad-area InGaN laser diode can be used, and also an InGaNAs laser diode or a GaNAs laser diode can be used. Further, the above-described light sources may have a configuration in which a light emitting body, such as a light emitting diode, is used.

The illumination optical system 30a is provided with a fluorescent body 210 in addition to the illumination lens 32, and blue laser light or blue-green laser light from the light guide 25 enters the fluorescent body 210. The fluorescent body 210 is excited by the blue laser light to emit fluorescent light. Further, part of the blue laser light passes through the fluorescent body 210 without exciting the fluorescent body 210. The blue-green laser light passes through the fluorescent body 210 without exciting the fluorescent body 210. Light that exits from the fluorescent body 210 passes through the illumination lens 32 to illuminate the interior of the body that is an observation target.

Figure 27:
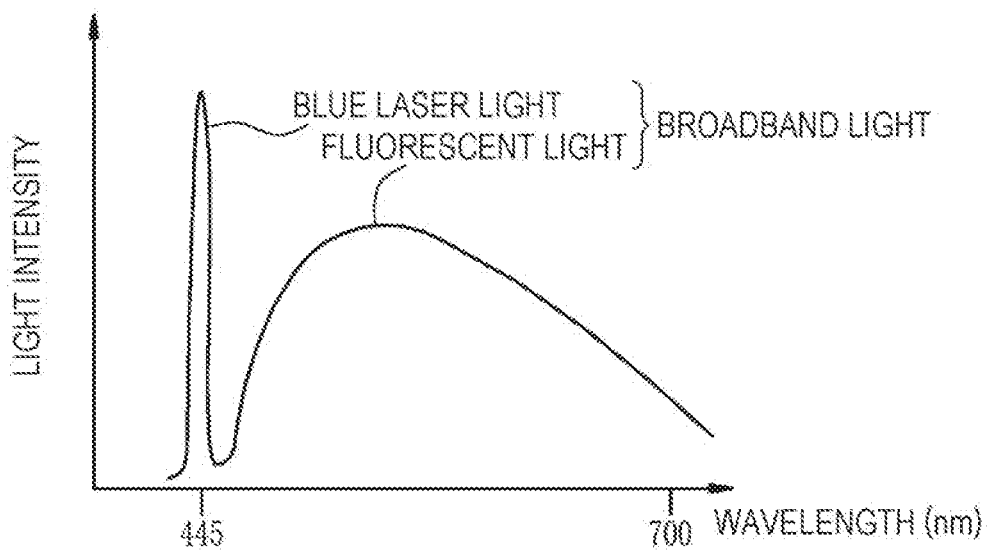
FIG. 27 is a graph illustrating the spectrum of broadband light.

Here, in the normal mode, the blue laser light mainly enters the fluorescent body, and therefore, an observation target is illuminated with broadband light, in which the blue laser light and fluorescent light emitted from the fluorescent body excited by the blue laser light are multiplexed, as normal light as illustrated in FIG. 27. When image capturing of the observation target illuminated with the normal light is performed with the image sensor 44, a normal image formed of Bc image signals, Gc image signals, and Rc image signals is obtained.

Figure 28:
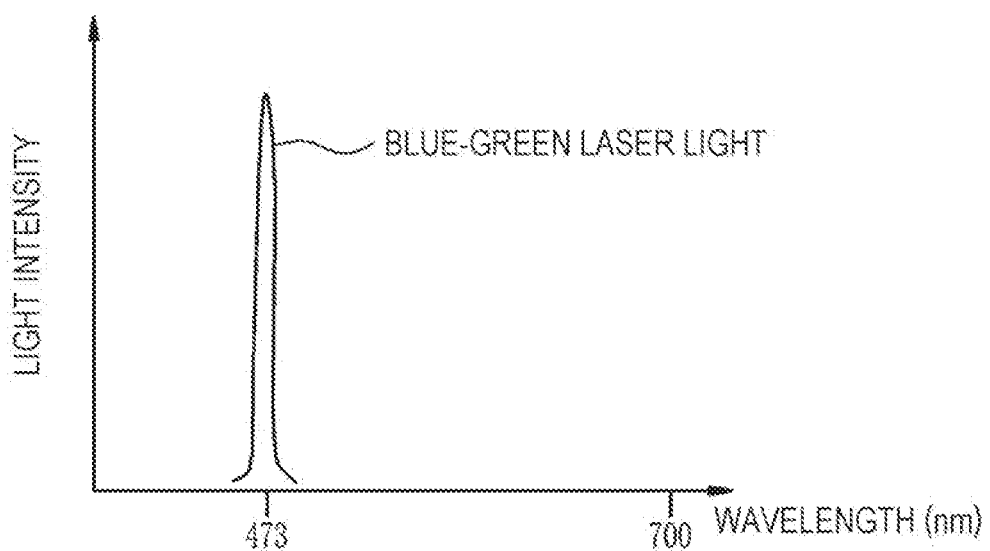
FIG. 28 is a graph illustrating the spectrum of blue-green laser light.

On the other hand, in the oxygen saturation mode and the calibration mode, when the blue laser light enters the fluorescent body, an observation target is illuminated with the broadband light illustrated in FIG. 27. When the blue-green laser light enters the fluorescent body, most of the blue-green laser light is not absorbed into the fluorescent body, and therefore, an observation target is illuminated with the blue-green laser light substantially directly, as illustrated in FIG. 28.

In the oxygen saturation mode, a signal output from each B pixel of the image sensor 44 during illumination with the blue-green laser light corresponds to the B1 image signal of the first embodiment described above. Further, a signal output form each B pixel of the image sensor 44 during illumination with the broadband light corresponds to the B2 image signal of the first embodiment described above, a signal output from each G pixel thereof corresponds to the G2 image signal of the first embodiment described above, and a signal output from each R pixel thereof corresponds to the R2 image signal of the first embodiment described above. On the basis of the B1 image signals, the B2 image signals, the G2 image signals, and the R2 image signals, the oxygen saturation levels are calculated with a method similar to that in the first embodiment.

In the calibration mode, a signal output from each B pixel of the image sensor 44 during illumination with the blue-green laser light corresponds to the Bq image signal of the first embodiment described above. Further, a signal output from each B pixel of the image sensor 44 during illumination with the broadband light corresponds to the Bp image signal of the first embodiment described above, a signal output from each G pixel thereof corresponds to the Gr image signal of the first embodiment described above, and a signal output from each R pixel thereof corresponds to the Rs image signal of the first embodiment described above. On the basis of the Bp image signals, the Bq image signals, the Gr image signals, and the Rs image signals, the residual liquid amount is calculated or the correlations are corrected with a method similar to that in the first embodiment.

Note that, as the fluorescent body 210, it is preferable to use a fluorescent body formed by including a plurality of types of fluorescent bodies (for example, fluorescent bodies such as a YKG fluorescent body or a BAM ($BaMgAl_{10}O_{17}$) fluorescent body) that absorb part of the blue laser light and are excited to emit green to yellow light. When a semiconductor light emitting element is used as an excitation light source of the fluorescent body 210 as in this example configuration, white light having high intensity can be obtained with a high light emission efficiency, the intensity of the white light can be easily adjusted, and changes in the color temperature and chromaticity of the white light can be made smaller.

Note that, in the embodiments described above, to correct the correlations in the calibration mode, the first blue light BS in a wavelength range of 450±10 nm is used; however, light in a wavelength range in which the light absorption coefficient of oxyhemoglobin and that of reduced hemoglobin are the same and the light absorption coefficient of a yellow pigment is larger than that in the other wavelength range may be used. For example, instead of the first blue light BS, green narrowband light in a wavelength range of 500±10 nm may be used.

Note that, in the embodiments described above, the residual liquid amount of a substance having a yellow pigment is calculated; however, the residual liquid amount of a blue pigment in a blue color series, such as indigo carmine or crystal violet, may be calculated by using a similar residual liquid amount calculation method.

REFERENCE SIGNS LIST 2 observation window
3 illumination window
4 air/water supply nozzle
5 forceps outlet
6 residual liquid removal part
10 endoscope system
12 endoscope
12a insertion part
12b operation part
12c bending part
12d distal end part
12e angle knob
12f mode switching SW
12g still-image obtainment instruction part
12h air/water supply button
12i suction button
14 light source device
16 processor device
18 monitor
19 console
20 light source
20a BS-LED
20b BL-LED
20c G-LED
20d R-LED
21 light source control unit
23 optical path coupling unit
25 light guide
30a illumination optical system
30b image capture optical system
32 illumination lens
42 object lens
44 image sensor
45 image capture control unit
46 CDS/AGC circuit
48 A/D converter
50 image signal obtaining unit
52 DSP
54 noise reduction unit
56 image processing switch unit
58 normal image generation unit
60 oxygen saturation image generation unit
62 calibration processing unit
64 video signal generation unit
70 signal ratio calculation unit
72 correlation storage unit
74 oxygen saturation level calculation unit
76 image generation unit
80, 81 graph
82, 83 isopleth
84 baseline information calculation unit
85 baseline correction value calculation unit
85a reference baseline information storage unit
86 residual liquid amount calculation unit
86a residual liquid amount storage unit
87 residual liquid removal ratio/residual ratio calculation unit
88 first residual liquid image generation unit
89 second residual liquid image generation unit
90 oxygen saturation level calculation accuracy conversion unit
91 residual liquid removal guidance image generation unit
92 residual liquid removal instruction unit
93 correlation correction value calculation unit
94 correlation correction unit
95 reference line
96 actual measurement line
97 guidance
98 message
100 endoscope system
102 broadband light source
104 rotating filter
105 filter switch unit
106 image sensor
108 inner filter
108a B1 filter
108b G filter
108c R filter
109 outer filter
109a B1 filter
109b B2 filter
109c G filter
109d R filter
200 endoscope system
204 blue laser light source (445LD)
206 blue-green laser light source (473LD)
208 light source control unit
210 fluorescent body

What is claimed is:

1. An endoscope system comprising: a light source; an endoscope that performs image capturing of an observation target onto which illumination light emitted from the light source is radiated; and a processor device that performs system control and image processing, the endoscope system comprising:
   an image signal obtaining unit that obtains image signals in a plurality of wavelength ranges obtained by image capturing of the observation target;
   a baseline information calculation unit that calculates, on the basis of the image signals in the plurality of wavelength ranges, baseline information that is information regarding a light scattering characteristic or a light absorption characteristic of the observation target and that does not depend on specific biological information;
   a reference baseline information storage unit that stores in advance reference baseline information that is a reference for evaluating the baseline information;
   a baseline correction value calculation unit that calculates a baseline correction value for adjusting the baseline information to the reference baseline information; and
   a residual liquid information calculation unit that calculates residual liquid information regarding a residual liquid included in the observation target from the baseline correction value,
   wherein the residual liquid information calculation unit includes a residual liquid amount calculation unit that calculates a residual liquid amount of the residual liquid as the residual liquid information.

2. The endoscope system according to claim 1, further comprising a first residual liquid image generation unit that generates a first residual liquid image representing distribution of the residual liquid information.

3. The endoscope system according to claim 1, further comprising a second residual liquid image generation unit that generates a second residual liquid image representing the residual liquid information by a numerical value or an indicator.

4. The endoscope system according to claim 1, further comprising:
   a biological information calculation unit that calculates the specific biological information; and
   a biological information calculation accuracy conversion unit that converts the residual liquid information to a calculation accuracy of the specific biological information.

5. The endoscope system according to claim 1, further comprising a residual liquid removal guidance image generation unit that generates, in accordance with the residual liquid information, a residual liquid removal guidance image for urging removal of the residual liquid.

6. The endoscope system according to claim 1, further comprising a residual liquid removal instruction unit that instructs, in accordance with the residual liquid information, a residual liquid removal part to remove the residual liquid, the residual liquid removal part being a part for removing the residual liquid.

7. The endoscope system according to claim 6, wherein the residual liquid removal instruction unit sets a residual liquid removal condition in accordance with the residual liquid information.

8. The endoscope system according to claim 1, wherein the residual liquid amount calculation unit calculates the residual liquid amount having an increased value as the baseline correction value increases.

9. The endoscope system according to claim 1, further comprising
   a residual liquid removal part for removing the residual liquid, wherein
   the residual liquid information calculation unit includes a residual liquid removal ratio/residual ratio calculation unit that calculates a pre-residual-liquid-removal residual liquid amount before removal of the residual liquid and a post-residual-liquid-removal residual liquid amount after removal of the residual liquid and that calculates a removal ratio of the residual liquid and/or a residual ratio of the residual liquid as the residual liquid information from the pre-residual-liquid-removal residual liquid amount and the post-residual-liquid-removal residual liquid amount.

10. The endoscope system according to claim 6, wherein the residual liquid removal part removes the residual liquid by at least any of water supply, air supply, or suction.

11. The endoscope system according to claim 1, wherein the image signals in the plurality of wavelength ranges include a first image signal that corresponds to a first wavelength range in which a light absorption amount changes in accordance with a change in the specific biological information, a second image signal that corresponds to a second wavelength range that is a wavelength range different from the first wavelength range and in which a light absorption amount changes due to a factor other than a change in the specific biological information, a third image signal that corresponds to a third wavelength range that is longer in wavelength than the first wavelength range and the second wavelength range and in which a light absorption amount changes in accordance with a blood volume, and a fourth image signal that corresponds to a fourth wavelength range that is longer in wavelength than the third wavelength range.

12. The endoscope system according to claim 11, wherein the first image signal, the second image signal, the third image signal, and the fourth image signal are obtained by multi-frame image capturing of the observation target.

13. The endoscope system according to claim 1, wherein the specific biological information changes in accordance with a concentration of a hemoglobin pigment included in the observation target.

14. The endoscope system according to claim 13, wherein the specific biological information is any of an oxygen saturation level, a blood vessel density, a blood vessel depth, a blood vessel thickness, or a blood concentration.

15. The endoscope system according to claim 1, wherein the baseline information is information that changes in accordance with a concentration of a pigment other than hemoglobin included in the observation target.

16. The endoscope system according to claim 15 wherein the pigment other than hemoglobin is a pigment that is included in a living body or that is used at a time of endoscopic observation.

17. The endoscope system according to claim 16, wherein the pigment other than hemoglobin includes at least any of a yellow pigment, a bluish violet series pigment, a brown series pigment, or a white pigment.

18. The endoscope system according to claim 17, wherein the yellow pigment is bilirubin or stercobilin, the bluish violet series pigment is indigo carmine or crystal violet, the brown series pigment is Lugol, and the white pigment is acetic acid.

19. The endoscope system according to claim 1, wherein the reference baseline information is baseline information obtained in a case where an effect of pigment other than hemoglobin does not exist.

20. An operation method for an endoscope system comprising a light source, an endoscope that performs image capturing of an observation target onto which illumination light emitted from the light source is radiated, and a processor device that performs system control and image processing, the operation method comprising:
   a step of obtaining image signals in a plurality of wavelength ranges obtained by image capturing of the observation target, by an image signal obtaining unit;
   a step of calculating, on the basis of the image signals in the plurality of wavelength ranges, baseline information that is information regarding a light scattering characteristic or a light absorption characteristic of the observation target and that does not depend on specific biological information, by a baseline information calculation unit;
   a step of calculating a baseline correction value for adjusting the baseline information to reference baseline information that is a reference for evaluating the baseline information, by a baseline correction value calculation unit; and
   a step of calculating a residual liquid amount of the residual liquid as residual liquid information regarding a residual liquid included in the observation target from the baseline correction value, by a residual liquid information calculation unit.

* * * * *